(12) United States Patent
Schneider

(10) Patent No.: US 8,225,837 B2
(45) Date of Patent: Jul. 24, 2012

(54) APPARATUS FOR MAKING ABSORBENT ARTICLES HAVING SIDE SEAMS

(75) Inventor: Uwe Schneider, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 676 days.

(21) Appl. No.: 12/348,616

(22) Filed: Jan. 5, 2009

(65) Prior Publication Data

US 2010/0172723 A1    Jul. 8, 2010

(51) Int. Cl.
*A61F 13/15* (2006.01)
(52) U.S. Cl. .................... 156/443; 156/539
(58) Field of Classification Search .............. None
See application file for complete search history.

(56) References Cited

U.S. PATENT DOCUMENTS

| | | | |
|---|---|---|---|
| RE26,151 E | | 1/1967 | Duncan et al. |
| 3,653,285 A | * | 4/1972 | Yoshikawa et al. ............ 82/101 |
| 3,860,003 A | | 1/1975 | Buell |
| 4,515,595 A | | 5/1985 | Kievit et al. |
| 4,573,986 A | | 3/1986 | Minetola et al. |
| 4,610,678 A | | 9/1986 | Weisman et al. |
| 4,673,402 A | | 6/1987 | Weisman et al. |
| 4,695,278 A | | 9/1987 | Lawson |
| 4,834,735 A | | 5/1989 | Alemany et al. |
| 4,842,666 A | | 6/1989 | Werenicz |
| 4,888,231 A | | 12/1989 | Angstadt |
| 4,909,803 A | | 3/1990 | Aziz et al. |
| 5,151,092 A | | 9/1992 | Buell et al. |
| 5,779,831 A | | 7/1998 | Schmitz |
| 7,013,941 B2 | * | 3/2006 | Schneider et al. ............ 156/443 |
| 7,322,925 B2 | | 1/2008 | Couillard et al. |
| 2007/0137011 A1 | * | 6/2007 | Couillard et al. ............... 28/100 |
| 2008/0083489 A1 | | 4/2008 | Schneider |

FOREIGN PATENT DOCUMENTS

| | | |
|---|---|---|
| EP | 0 717 971 A1 | 6/1996 |
| EP | 0 717 972 A1 | 6/1996 |
| WO | WO 03/051248 | 6/2003 |
| WO | WO 2004/062541 | 7/2004 |
| WO | WO 2007/070113 | 6/2007 |

OTHER PUBLICATIONS

International Search Report dated Apr. 1, 2010, 4 pages.

* cited by examiner

*Primary Examiner* — John L. Goff
*Assistant Examiner* — Barbara J. Musser
(74) *Attorney, Agent, or Firm* — Charles R. Matson

(57) ABSTRACT

The present disclosure relates to methods and apparatuses for manufacturing absorbent articles, and more particularly, apparatuses and methods utilizing multiple processing stations for processing absorbent articles and being configurable to move along various predetermined travel paths defined by radii that may be constant or variable. Particular embodiments of apparatuses and methods of manufacture include a processing wheel having a plurality of processing stations which orbit around a rotation axis. The processing stations may be configured to perform various types of operations associated with the manufacture of absorbent articles while the processing stations orbit around the rotation axis. The processing wheel can be configured to adjust the path along which the processing stations orbit as the processing wheel rotates around the rotation axis. As such, the orbit path can be adjusted to accommodate the manufacture of different sized blanks without the need to physically move or relocate and realign other process apparatuses, such as for example, sealing stations.

5 Claims, 14 Drawing Sheets

US 8,225,837 B2

APPARATUS FOR MAKING ABSORBENT ARTICLES HAVING SIDE SEAMS

FIELD OF THE INVENTION

The present disclosure relates to methods and apparatuses for manufacturing absorbent articles, and more particularly, apparatuses and methods utilizing multiple rotating stations for processing absorbent articles and being configurable to move along various predetermined paths defined by varying radii.

BACKGROUND OF THE INVENTION

Infants and other incontinent individuals wear disposable absorbent articles such as diapers to absorb and retain urine and other body exudates. Absorbent articles may function both to contain the discharged materials and to isolate these materials from the body of the wearer and from the wearer's garments and bed clothing.

Diapers can be configured to fit on a wearer's body in various ways. For example, some diaper may be configured as pull-on pant-type diapers or training pants. Diapers, such as training pants, may be used with infants prior to and/or during toilet training. Training pants may be configured with a "closed" chassis configuration, in which the chassis is adapted to be pulled on over the legs and lower torso of the wearer without any additional fastening steps.

Closed chassis diapers may be manufactured with a front ear being seamed to a back ear to form the closed chassis. In some configurations, closed chassis diapers may also have manually tearable side seams. The side seams may be configured as butt-type seams or overlapping side seams.

During the manufacturing process, a closed chassis diaper may be manufactured from a blank cut to a particular configuration and size. Manufacturing processes may involve some type of sealing step to create side seams in the diapers. For example, after being fully assembled, the blank may be folded along a central transverse area and the sides of the front and rear panels are seamed together to form a closed chassis diaper. In other processes, the side seams may be formed by folding the chassis in a crotch portion so that longitudinal side regions of the front portion and rear portion are superposed to form seaming areas, which are then treated with ultrasonic energy to sever the material in the seaming area in a first area while simultaneously bonding the material of the seaming area in a marginal area adjacent the first area to form a flangeless seam.

In some manufacturing configurations, the seaming and folding operations may be performed automatically on a processing wheel having a plurality of folding stations and associated seaming mechanisms. Various types of such processing wheels have been described in U.S. Patent Publication No. 2008/0083489 and U.S. Pat. Nos. 5,779,831 and 7,322,925. The processing wheels provide the ability to produce training pants a high rate of speed. However, reconfiguring various components of the processing wheel to change manufacturing operations for different sizes of absorbent articles can be onerous. For example, some components of the processing wheel may require realignment, which can be time consuming and expensive. For instance, different size folding stations may be needed to accommodate a different sized diaper. Such different sized folding stations may need to be realigned with the seaming stations. In addition, different sized folding stations may also require changes in the physical locations of operating stations, such as the discharge station, located adjacent the processing wheel.

SUMMARY OF THE INVENTION

Aspects of the present disclosure relate to methods and apparatuses for manufacturing absorbent articles, and more particularly, apparatuses and methods utilizing multiple processing stations for processing absorbent articles and being configurable to move along various predetermined travel paths defined by radii that may be constant or variable.

In one form, an apparatus for making absorbent articles having side seams includes: a wheel adapted to rotate about a rotation axis; a first track defining a first circumferential shape surrounding the rotation axis, wherein the first track is stationary relative to the wheel; a second track defining a second circumferential shape surrounding the rotation axis, wherein the second track is stationary relative to the wheel; and a plurality of folding mechanisms disposed on the wheel. Each folding mechanism includes: a first follower member movably connected with the first track, the first follower member having a proximal end portion and a distal end portion; a carrier arm pivotally connected with the first follower member; a gripper member connected with the carrier arm; and a second follower member connected with the carrier arm and movably connected with the second track. As the wheel rotates, the distal end portion of the first follower member orbits in a first orbit path about the rotation axis in correspondence with the first circumferential shape, and the second follower member moves relative to the first follower member in correspondence with a relative radial distance between the first track and the second track.

In another form, an apparatus for making absorbent articles having side seams includes: a wheel adapted to rotate about a rotation axis; a first track defining a first circumferential shape surrounding the rotation axis, wherein the first track is stationary relative to the wheel; and a plurality of folding mechanisms disposed on the wheel. Each folding mechanism includes: a first follower member movably connected with the first track, the first follower member having a proximal end portion and a distal end portion; a carrier arm pivotally connected with the first follower member; and a gripper member connected with the carrier arm. As the wheel rotates, the carrier arm is selectively pivoted relative to the first follower member, and the distal end portion of the first follower member orbits in a first orbit path about the rotation axis in correspondence with the first circumferential shape, wherein the first orbit path is defined a varying distance from the rotation axis.

In yet another form, a method of making absorbent articles having side seams includes the steps of: cutting a web into discrete blanks; transferring the blanks onto folding mechanisms disposed on a wheel rotating around a rotation axis, wherein each folding mechanism comprises: a first follower member movably connected with the first track, the first follower member having a proximal end portion and a distal end portion, a carrier arm pivotally connected with the first follower member, a gripper member connected with the carrier arm, and a second follower member connected with the carrier arm and movably connected with the second track; moving the distal end portion of the first follower member in a first orbit path about the rotation axis in correspondence with a first circumferential shape defined by the first track; and actuating the folding mechanisms to fold the blanks by moving the second follower member relative to the first follower member in correspondence with a relative radial distance between the first track and the second track.

BRIEF DESCRIPTION OF THE DRAWINGS

FIG. 6b is a top elevational view of the processing station of FIG. 6a.

FIG. 8b is an outline showing the orbital path of the folding stations of FIG. 8a.

FIG. 9b is an outline showing the orbital path of the folding stations of FIG. 9a.

DETAILED DESCRIPTION OF THE INVENTION

Figure 1:
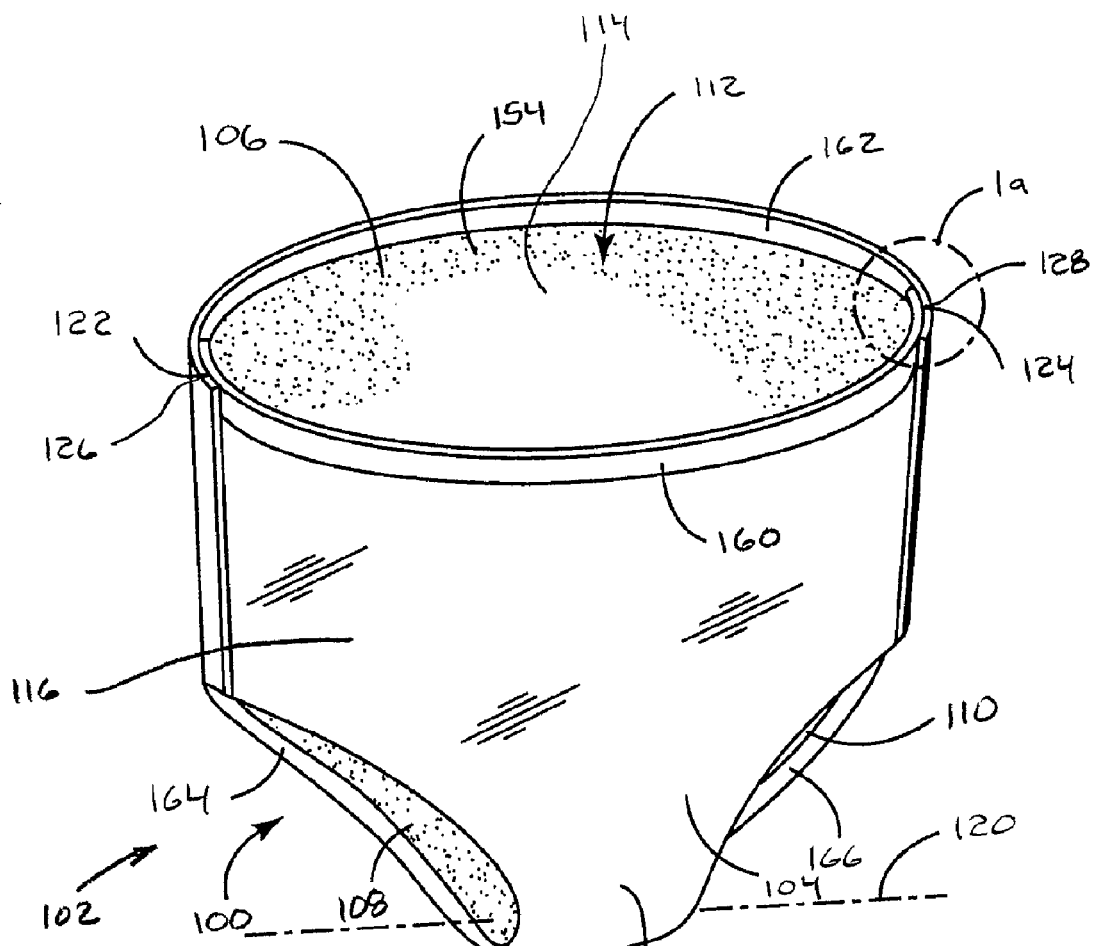
FIG. 1 shows an absorbent article having overlapping side seams.

The following term explanations may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

The term "body facing surface" refers to surfaces of absorbent articles and/or components thereof which face a wearer's body when the absorbent articles are worn, and the term "garment facing surface" refers to surfaces of absorbent articles and/or components thereof that face away from a wearer's body when the absorbent articles are worn. Absorbent articles and components thereof, including topsheets, backsheets, absorbent cores, and any individual materials of their components, have a body facing surface and a garment facing surface.

The term "disposed" is used herein to mean that an element (s) is formed (joined and positioned) in a particular place or position as a macro-unitary structure with other elements or as a separate element joined to another element.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a layer or layers or fibrous materials, films and foils such as plastic films or metallic foils that may be used alone or laminated to one or more web, layer, film and/or foil. As such, a web is a substrate.

The term "nonwoven" refers herein to a material made from continuous (long) filaments (fibers) and/or discontinuous (short) filaments (fibers) by processes such as spunbonding, meltblowing, and the like. Nonwovens do not have a woven or knitted filament pattern.

The term "machine direction" (MD) is used herein to refer to the direction of material flow through a process. The term "cross direction" (CD) is used herein to refer to a direction that is generally perpendicular to the machine direction.

As used herein the term "stretchable" refers to materials which can stretch to at least an elongated length of 105% on the upcurve of the hysteresis test at a load of about 400 gm/cm. The term "non-stretchable" refers to materials which cannot stretch to at least 5% on the upcurve of the hysteresis test at a load of about 400 gm/cm.

The terms "elastic" and "elastomeric" as used herein refer to any material that upon application of a biasing force, can stretch to an elongated length of at least about 110% of its relaxed, original length (i.e. can stretch to 10% more than its original length), without rupture or breakage, and upon release of the applied force, recovers at least about 40% of its elongation. For example, a material that has an initial length of 100 mm can extend at least to 110 mm, and upon removal of the force would retract to a length of 106 mm (40% recovery). The term "inelastic" refers herein to any material that does not fall within the definition of "elastic" above.

The term "extensible" as used herein refers to any material that upon application of a biasing force, can stretch to an elongated length of at least about 110% of its relaxed, original length (i.e. can stretch to 10%), without rupture or breakage, and upon release of the applied force, shows little recovery, less than about 40% of its elongation.

The terms "activating", "activation" or "mechanical activation" refer to the process of making a substrate, or an elastomeric laminate more extensible than it was prior to the process. "Live stretch" includes stretching elastic and bonding the stretched elastic to a substrate. After bonding, the stretched elastic is released causing it to contract, resulting in a "corrugated" substrate. The corrugated substrate can stretch as the corrugated portion is pulled to about the point that the substrate reaches at least one original flat dimension. However, if the substrate is also elastic, then the substrate can stretch beyond the relaxed length of the substrate prior to bonding with the elastic. The elastic is stretched at least 25% of its relaxed length when it is bonded to the substrate.

Aspects of the present disclosure relate to methods and apparatuses for manufacturing absorbent articles, and more particularly, apparatuses and methods utilizing multiple processing stations for processing absorbent articles and being configurable to move along various predetermined travel paths defined by radii that may be constant or variable. Particular embodiments of apparatuses and methods of manufacture disclosed herein include a processing wheel having a plurality of processing stations which orbit around a rotation axis. The processing stations may be configured to perform various types of operations associated with the manufacture of absorbent articles while the processing stations orbit around the rotation axis. For example, in some embodiments, separate pre-forms, or blanks, from which absorbent articles are formed, may be transferred to the orbiting processing stations from another apparatus used in the manufacturing process, such as an anvil roll. As the processing stations move along an orbit path, the processing stations may perform various operations, such as folding the blanks and superimposing sealing areas on the folded blanks. The processing stations may also move the sealing areas into a position to a desired alignment with a sealing station where the sealing areas are connected. Once the processing stations have performed the required operations, the folded blanks in the form of absorbent articles may be moved from the processing wheel to another apparatus used in the manufacturing operation. In accordance with the present disclosure, the processing wheel can be configured to adjust the path along which the processing stations orbit as the processing wheel rotates around the rotation axis. As such, the orbit path can be adjusted to accommodate the manufacture of different sized blanks without the need to physically move or relocate and realign other process apparatuses, such as for example, sealing stations.

With reference to FIGS. 1-4, a description of various types of articles that may be produced in accordance with the methods and apparatuses disclosed herein is provided below to provide a context for subsequent descriptions relating to the operation and structural features embodiments of the processing wheel and processing stations and associated manufacturing processes. Although the following description refers to disposable absorbent articles, in which a backsheet, an absorbent core, and a liquid permeable topsheet are combined to form an integral structure, it is to be appreciated that various types of articles may be produced in accordance with the methods and apparatuses described herein. As such, absorbent articles referred to herein may include a single layer or multiple layers of woven or nonwoven material and may include a thermoplastic film. In some instances, the articles may be constructed as a reusable diaper holder that is to be used in combination with a disposable absorbent insert core.

Figure 2:
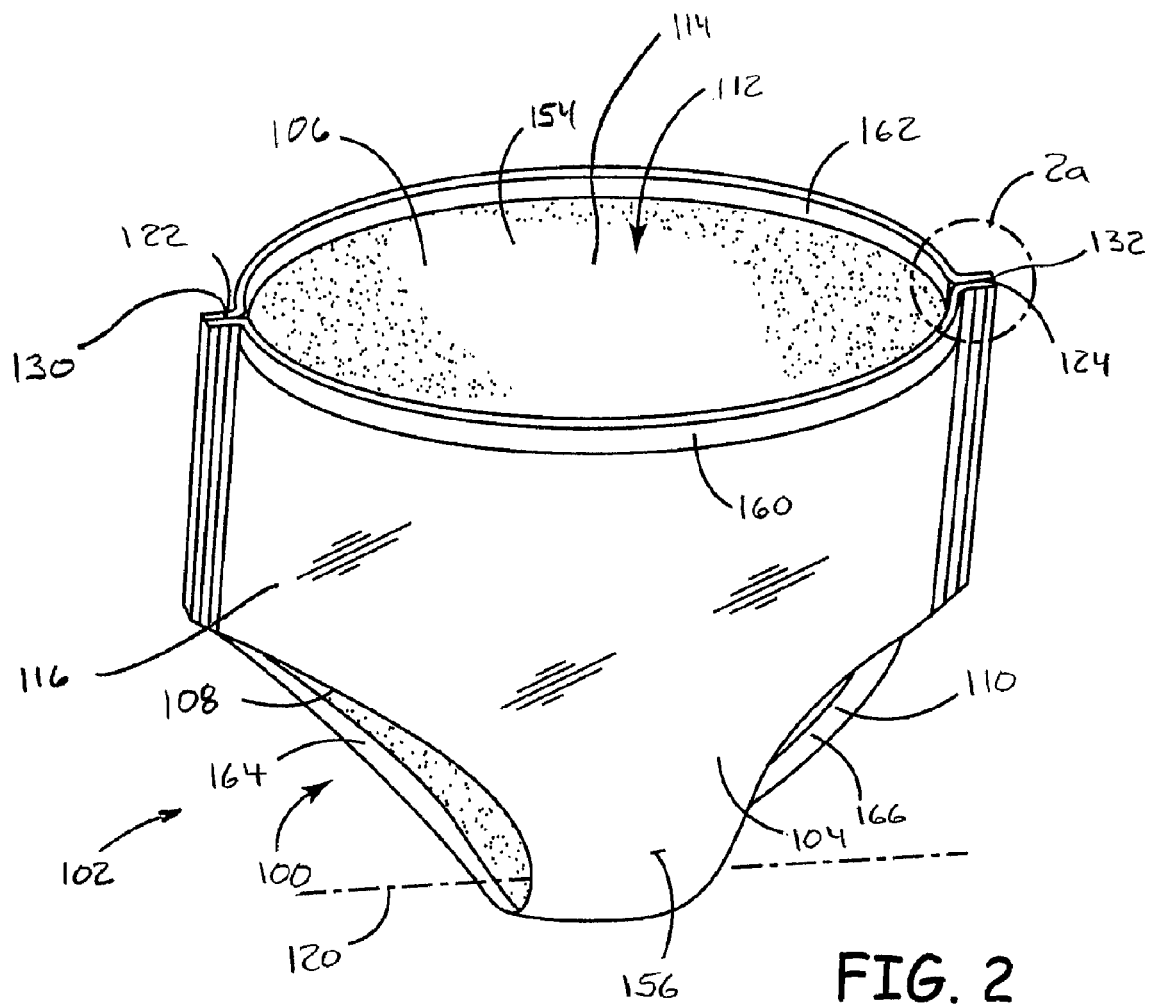
FIG. 2 shows an article having butt-type side seams.

FIGS. 1 and 2 show an absorbent article 100, which may be in the form of a diaper 102 illustrated as a pull-on type diaper, having a front panel 104 and a back panel 106 joined together to define leg openings 108, 110 and a waist opening 112. The diaper 102 also includes an inner, body facing surface 114, and an outer, garment facing surface 116. During the manufacturing process, the absorbent article 100 may be made from a pre-form, or blank 118, that is folded along a transverse center line 120 and having side seams 122, 124 connect the front panel and back panel together. The pre-form 118 is alternatively referred to herein as a blank 118. As discussed in more detail below, embodiments of a processing wheel, and more particularly, processing stations on a processing wheel fold the blanks 118 and position the folded blanks for connection of the side seams 122, 124.

Figure 1A:
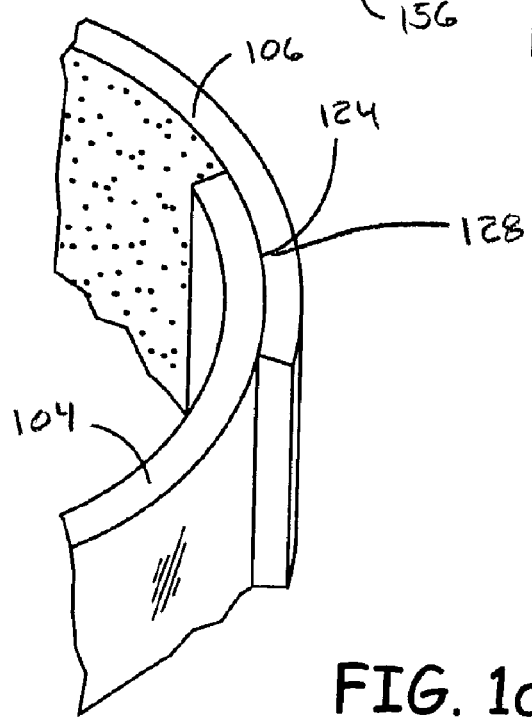
FIG. 1a shows a detailed view of a side seam of FIG. 1.
Figure 2A:
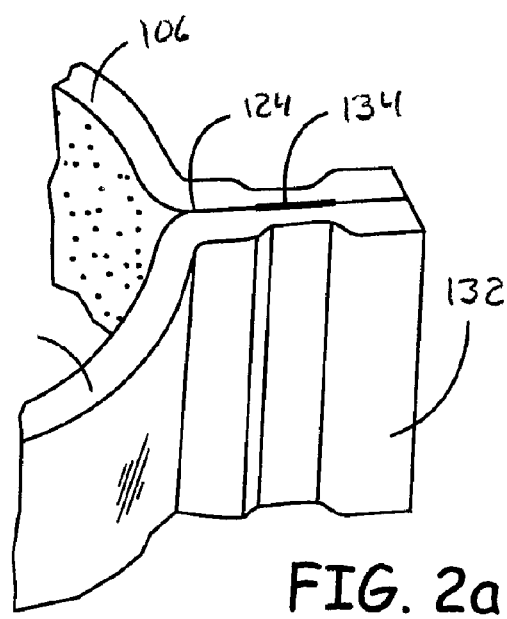
FIG. 2a shows a detailed view of a side seam of FIG. 2.

It is to be appreciated that various configurations of side seams may be used to connect the front and back panels together. For example, the side seams 122, 124 shown in FIGS. 1 and 1a are configured as overlapping side seams 126, 128, which are formed by overlapping portions of the front panel 104 and the back panel 106. Overlapping side seams may have favorable characteristics with respect to shear strength (in the plane of the front and back panels) and may be configured to be easily torn apart when removing an article from the wearer. FIGS. 2 and 2a show the absorbent article 100 having side seams 122, 124 in the form of outwardly located butt-type seams 130, 132. The butt-type seams 130, 132 are formed by folding the pre-form 118, along the transverse center line 124 and superimposing sealing areas that are located on wearer facing surfaces of the blank in a face-to-face relationship. As shown in FIGS. 2 and 2a, sealing lines 134 of the butt-type seams 130, 132 may be located inboard from the outer periphery, leaving outermost edges of the seam unattached to help create a relatively soft edge. It should be appreciated that the butt-type side seams 130, 132 may be inwardly oriented, or located on the inside of the absorbent article 100.

It is to be appreciated that overlapping seams 126, 128 and butt-type seams 130, 132 may be formed with various types of connection methods, including for example, pressure bonding, ultrasonic bonding, heat sealing, adhesive attachment, and mechanical attachment. Adhesive and mechanical attachments may include, for example, patches of hook-type and loop-type material. Such patches may be located parallel to the sides seams and may be located perpendicular to the seams. The side seams 122, 124 may be joined by adhesive tape extending perpendicularly to the seams. The sealing mechanism or adhesive tape may provide for a resealable side seam and may be attached by the manufacturer to form the absorbent article 100. After the absorbent article 100 has been attached on a wearer, the side seams 122, 124 can be unfastened for inspection of the inside of the article and can after inspection be re-closed by the user for further use.

Figure 3:
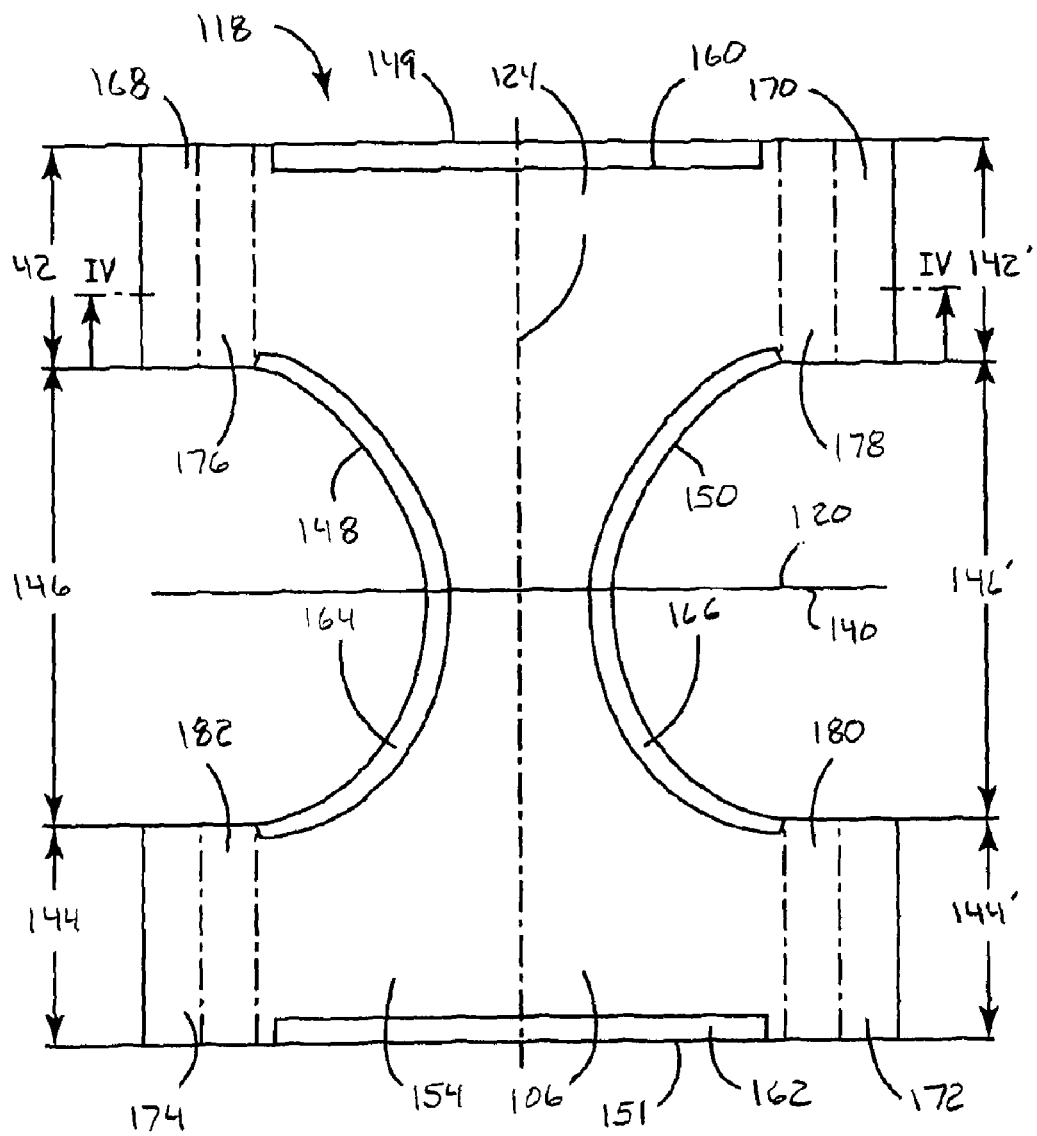
FIG. 3 shows a top plan view of a blank for forming an absorbent article having side seams.
Figure 4:
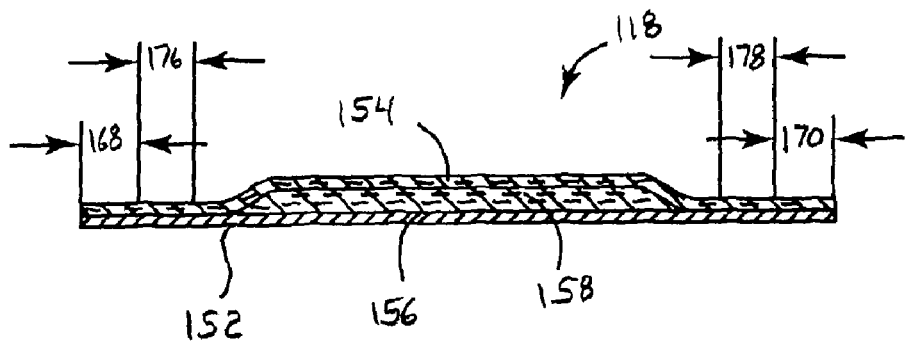
FIG. 4 shows a cross-sectional view of the blank of FIG. 3 taken along line IV-IV.

As mentioned above, absorbent articles 100 having side seams 122, 124 may be formed from a blank 118 during the manufacturing process. For the purposes of a specific illustration, FIGS. 3 and 4 show an example blank 118 that may be used to form an absorbent article 100 having side seams 122, 124. In general, the blank 118 shown in FIG. 3 is a representation of the absorbent articles 100 of FIGS. 1 and 2 in the form of diapers 102 prior to joining of the front panel 104 and the rear panel 106. As such, the blank 118 shown in FIG. 3 along may be folded along the transverse center line 120 and the back panel 106 and the front panel 104 connected with overlapping seams 126, 128 or butt-type seams 130, 132 as shown in FIGS. 1 and 2.

FIG. 3 is a plan view of the blank 118 including a chassis 136 shown in a flat, unfolded condition, with the portion of the chassis that faces toward a wearer oriented towards the viewer. FIG. 4 shows a cross-sectional view of the blank 17 shown in FIG. 3. To provide a frame of reference for the present discussion, the chassis 136 is shown with a longitudinal axis 138 and a lateral axis 140. As shown in the FIG. 3, the lateral axis 140 may correspond with the transverse center line 120. The chassis 136 is shown as having a first waist region 142, 142'; a second waist region 144, 144'; and a crotch region 146, 146' disposed intermediate the first and second waist regions. The periphery of the diaper is defined by a pair of longitudinally extending side edges 148, 150; a first outer edge 149 extending laterally adjacent the first waist region 142; and a second outer edge 151 extending laterally adjacent the second waist region 144. A length, $L_{BLANK}$, of the blank is defined by a longitudinal distance between the first outer edge 149 and second outer edge 151. A length, $L_{BLANK}$, defined by relatively large absorbent articles may be longer than a length, $L_{BLANK}$, defined by relatively small absorbent articles.

Still referring to FIG. 3, the longitudinal edges 148, 150 extend generally in the direction of the longitudinal center line 138 and may curve to define cut-out regions that form portions of the leg openings 108, 110 of the absorbent article 100. The chassis 136 may also include an outer covering layer 152 including a topsheet 154 and a backsheet 156, and an absorbent core 158 disposed between a portion of the topsheet and the backsheet. It is to be appreciated that any one or more of the regions of the chassis may be stretchable and may include various types of elastomeric materials and/or laminates. As such, the diaper 102 may be configured to adapt to a specific wearer's anatomy upon application and to maintain coordination with the wearer's anatomy during wear. The blank 118 may further comprise waist elastics 160, 162 and leg elastics 164, 166. As shown in FIGS. 3 and 4, the longitudinal edges 148, 150 adjacent the first waist region 142, 142' and the second waist region 144, 144' include sealing areas 168, 170, 172, 174, which may comprise a thermoplastic material. In addition, a gripping area 176, 178, 180, 182 may be provided adjacent each sealing area 168, 170, 172, 174. The gripping and sealing areas are discussed in more detail below in the context of describing the operation of embodiments of the processing wheels.

As discussed above, the absorbent article may include an absorbent core 158, which may comprise any absorbent material capable of absorbing and retaining liquids such as urine and other body exudates. Exemplary but not limiting absorbent structures for use as the absorbent core 158 are described in U.S. Pat. Nos. 4,610,678, 4,673,402, 4,888,231, and 4,834,735, each herein incorporated by reference. The absorbent core 158 may be manufactured in a wide variety of sizes and shapes (e.g., rectangular, hourglass, "T"-shaped, asymmetric, etc.), and from a wide variety of liquid-absorbent materials commonly used in disposable diapers and other absorbent articles. The absorbent core may also include multiple layers of absorbent material, each having individual liquid acquisition, acquisition/distribution, or storage/redistribution characteristics, as well as individual shape, width, length, and thickness characteristics. The number and placement of absorbent layers may be varied to achieve desired characteristics such as thinness, softness, flexibility, or beneficial liquid acquisition, distribution, and storage rates, as well as capacity and storage rates, wearer comfort, etc. The components or members of the absorbent core may include laminates or combinations of several sheets or webs of materials. In general, the absorbent core may be made of any suitable absorbent material or combination of materials.

As shown in FIG. 4, the backsheet 156 may be positioned adjacent a garment facing surface of the absorbent core 158 and may be joined thereto in any suitable manner, including but not limited to adhesive, heat bonds, pressure bonds, ultrasonic bonds, dynamic mechanical bonds, or any other suitable attachment. See, e.g., U.S. Pat. Nos. 4,573,986 and 4,842,666, each herein incorporated by reference. Some portion or all of the backsheet 156 may be generally impervious to liquids (e.g., urine) and may be manufactured from a thin plastic film, although other flexible liquid impervious materials may also be used. The backsheet 156 may thus comprise a woven or nonwoven material, polymeric films such as thermoplastic films of polyethylene or polypropylene, composite materials such as a film-coated nonwoven material, or any other suitable material. The backsheet 156 may be embossed and/or matte finished to provide a more cloth-like appearance. Further, the backsheet 156 may permit vapors to escape from the absorbent core 158 (i.e., breathable) while preventing exudates from passing through the backsheet 156.

As shown in FIG. 4, the topsheet 154 is positioned adjacent a body facing surface of the absorbent core 158 and may be joined thereto and/or to the backsheet 156. Suitable attachment methods are described with respect to joining the backsheet 156 to the absorbent core 158. The topsheet 154 may be compliant, soft feeling, and non-irritating to the wearer's skin. Generally, the topsheet 154 may be liquid pervious permitting liquids (e.g., urine) to readily penetrate through its thickness. A topsheet can be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Example woven and nonwoven materials can include natural fibers, e.g., wood or cotton fibers, synthetic fibers, e.g., polymeric fibers such as polyester, polypropylene, or polyethylene fibers, or a combination of natural and synthetic fibers. In one embodiment, the topsheet is made of a hydrophobic material to isolate the wearer's skin from liquids contained in the absorbent core that is treated on at least one side with a surfactant to allow liquids to readily penetrate therethrough. High loft nonwoven topsheets and apertured formed film topsheets may be used. Apertured formed films are pervious to bodily liquids, non-absorbent, and have a reduced tendency to allow liquids to pass through in a direction away from the absorbent core and thereby rewet the wearer's skin. Thus, the surface of the formed film that is in contact with the body remains dry, thereby reducing bodily soiling and creating a more comfortable feel for the wearer. The body-facing surface of the formed film topsheet can be hydrophilic, thereby helping bodily liquids transfer through the topsheet faster and diminishing the likelihood that liquid will flow off the topsheet rather than flowing into and being absorbed by the absorbent core. There are a number of manufacturing techniques that may be used to manufacture the topsheet 154. For example, the topsheet 154 may be a nonwoven web of fibers spunbonded, carded, wet-laid, meltblown, hydroentangled, thermally bonded, combinations of the above, or the like.

In some embodiments, an absorbent core structure without a topsheet may be used to provide desirable results, such as comfort and absorbency, as well as simplicity in manufacturing and material cost savings. For example, the body facing surface of the absorbent core may be made of liquid pervious, soft, compliant, non-irritating materials. Such an absorbent core may be used in combination with a backsheet to provide the desired comfort and absorbency in an absorbent article.

In some embodiments, the topsheet 154 and the backsheet 156 are coextensive and have length and width dimensions generally larger than those of the absorbent core 158. In other embodiments, the topsheet 154 may be slightly smaller than the backsheet 156. The size of the backsheet and/or topsheet may be guided by the size of the absorbent core and the article design selected.

As mentioned above, elastics, including waist elastics and leg elastics may be provided to exert a contracting force on the absorbent article so that the absorbent article configures more closely and more comfortably to the wearer. Elastic members for use in wait elastics and leg elastics can be assembled in a variety of well known configurations, such as those described generally in U.S. Pat. No. 3,860,003, herein incorporated by reference.

As shown in FIGS. 1-3, the disposable absorbent article 100 may comprise elasticized leg cuffs 164, 166 for providing improved containment of liquids and other body exudates. Each elasticized leg cuff may comprise several different embodiments for reducing the leakage of body exudates in the leg regions. The leg cuff can be and is sometimes also referred to as leg bands, side flaps, barrier cuffs, or elastic cuffs. Various cuffs, flaps, and openings are described in U.S. Pat. Nos. 3,860,003, 4,909,803, and 4,695,278, each of which is herein incorporated by reference.

As shown in FIGS. 1-3, the disposable absorbent article may comprise an elastic waist feature 160, 162 that provides improved fit and containment. The elastic waist feature is that portion or zone of the absorbent article which is intended to elastically expand and contract to dynamically fit the wearer's waist. The elastic waist feature may extend longitudinally outwardly from at least one of the waist edges of the absorbent core 158 and may generally form at least a portion of the end edges of the blank 118. Thus, waist elastics 160, 162 may be disposed adjacent either or both transverse edges 149, 151 to provide a waistband. Disposable absorbent articles may be constructed so as to have two elastic waist features 160, 162. For example, one elastic waist feature 149 may be positioned in the first waist region 142, 142' and one elastic waist feature 151 may be positioned in the second waist region 144, 144'. It should also be appreciated that diapers can be constructed with a single elastic waist feature. The waist elastics 160, 162 may be secured to the absorbent article in an elastically contractible condition so that, in a normally unrestrained configuration, the waist elastics effectively contract or gather the absorbent article. The elastics 160, 162 may also extend less than or equal the entire length of the transverse edges 149, 151 to provide an elastically contractible line. In one embodiment illustrated in U.S. Pat. No. 4,515,595, elastic waist elements extend across essentially the entire lateral width of a disposable diaper. Similar waistbands may be useful in designs wherein the elastic waist elements extend across only a portion of the lateral width of an absorbent article. While the elastic waist feature or any constituent elements can comprise a separate element affixed to the absorbent article, the elastic waist feature may be constructed as an extension of other elements of the diaper such as the backsheet 156 or the topsheet 154, or both the backsheet 156 and the topsheet 154. The elastic waistband may also be constructed in a number of different configurations including those described in U.S. Pat. Nos. 4,515,595 and 5,151,092, each incorporated herein by reference.

Figure 4A:
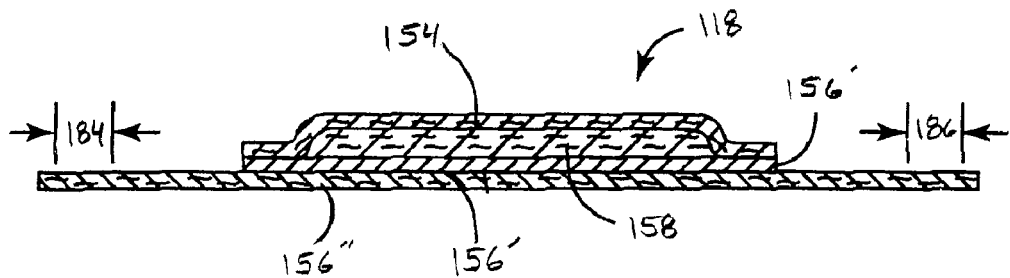
FIGS. 4a-4e show cross-sectional views of different embodiments of blanks for forming articles having side seams.
Figure 4B:
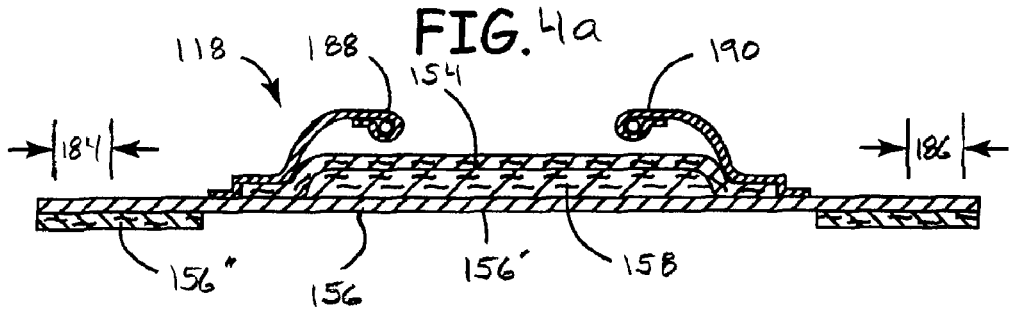
Figure 4C:
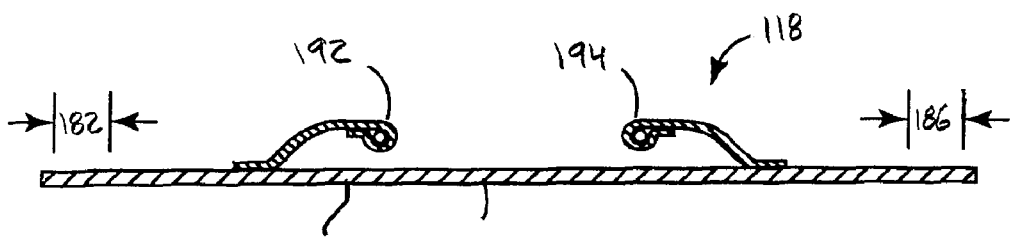
Figure 4D:
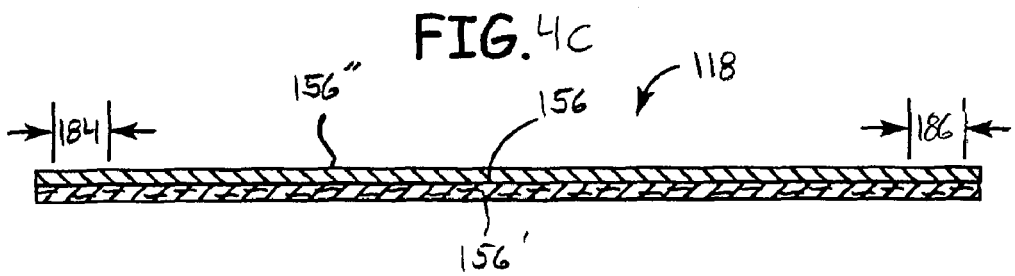
Figure 4E:
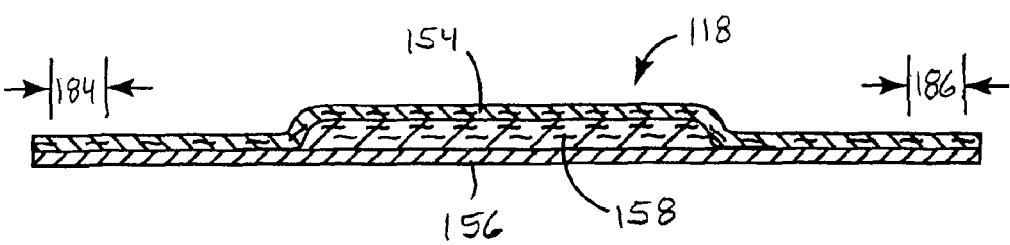

FIGS. 4a-4e illustrate different embodiments of blanks 118 that may be used with the disclosed methods and apparatuses. In particular, FIGS. 4a-4e show cross-sectional views along a cross-section that extends parallel to lateral axes of the blanks 118 and that cuts through two sealing areas 140, 142. The two sealing areas 140, 142 may correspond with the locations of the waist sealing areas 168, 170 or 172, 174 shown in FIGS. 3 and 4 or may be located in other areas. FIG. 4a shows an embodiment wherein the blank 118 from which the absorbent article 100 is formed comprises a topsheet 154, a backsheet 156, and a core 158 interposed between the topsheet and backsheet. The backsheet is formed by a thermoplastic film 156' and a non-woven outer layer 156". The thermoplastic film 156' is not coterminous with the non-woven outer layer 156", such that in each sealing area 140, 142 only two layers of the non-woven material 156" are present. The absorbent structure may also be made breathable through the use of regions of the non-woven material that are not covered by impermeable film 156'. In the embodiment of FIG. 4b, the blank 118 includes a thermoplastic film backsheet 156, 156' having panels of stretchable material attached thereto that form elasticized stand-up cuffs 188, 190 provided on each side of the core 158. In the embodiment of FIG. 4c, the blank 118 includes a reusable holder for absorbent insert cores. As such, the blank 118 includes a non-woven backsheet 156, 156" and two pocket-forming flaps 192, 194 between which a disposable insert core can be inserted, wherein the flaps 192, 194 help to hold the disposable insert core in position. FIG. 4d shows a blank 118 with a backsheet 156, which may include a laminate of two non-woven layers 156", 156", wherein both nonwoven layers extend into the sealing areas 184, 186 for improved strength of the side seams. It should be appreciated that the blank in FIG. 4d could also include a backsheet comprising a laminate of a nonwoven layer and a thermoplastic layer, or the backsheet could be any other suitable material or materials. FIG. 4e shows a blank 118 wherein both the topsheet 154 and the backsheet 156 extend into the sealing areas 184, 186 to form reinforced side seams.

Various types of articles, such as those discussed above with reference to FIGS. 1-4e, may be produced in accordance with the methods and apparatuses disclosed herein. In some embodiments, a continuous web may be cut into individual blanks, and the individual blanks are transferred to a processing wheel. More particularly, the individual blanks are transferred to corresponding processing stations moving along an orbit path as the processing wheel rotates. As the processing stations move along an orbit path, the processing stations may perform various operations, such as folding the blanks, superimposing sealing areas on the folded blanks, and sealing the side seams to form individual absorbent articles.

Figure 5:
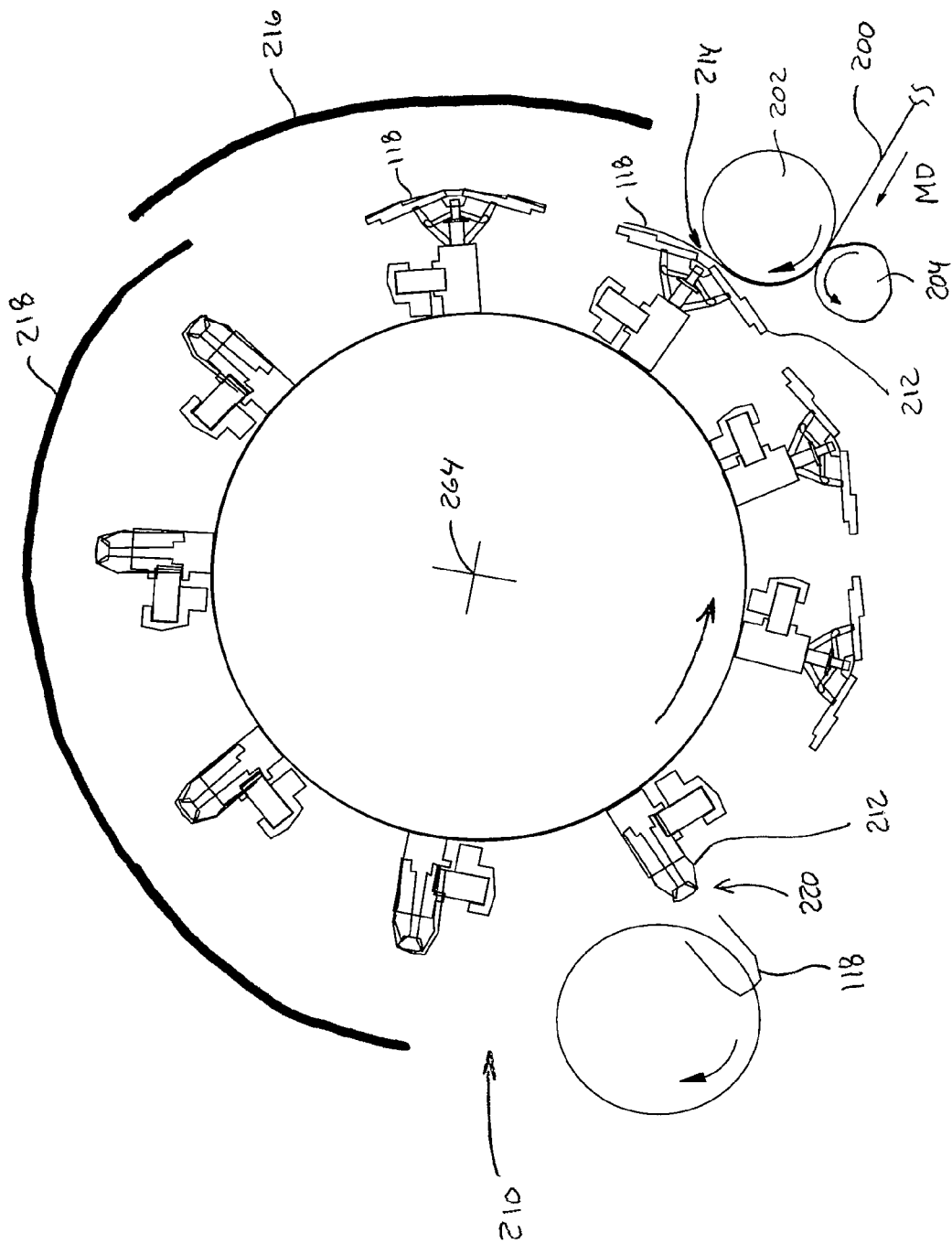
FIG. 5 a process diagram of a processing wheel for forming seamed articles.

FIG. 5 illustrates a schematic view of an example process for forming absorbent articles having side seams. As shown in FIG. 5, a continuous web 200 from which individual blanks 118 will be formed moves in a machine direction (MD) along a conveyor 202 from an upstream converting process wherein various absorbent article components may be combined with one or more advancing substrates of material. From the conveyor, the web 200 is transferred to a cutting station 204 that includes a final knife roll 204 and an anvil roll 206. The cutting station performs a final knife cut on continuous web 200, which separates the continuous web into individual blanks 118, such as shown in FIG. 3. The final knife cut separates the continuous web between a trailing edge of one blank and the leading edge of another blank. It is to be appreciated that various embodiments of cutting stations can be used other than those shown in FIG. 5. After the final knife cut, the individual blanks are transferred to a rotating processing wheel 210. As discussed in more detail below, the individual blanks 118 are transferred from the knife roll to individual processing stations 212 on the processing wheel 210 at a receiving location 214.

With reference to FIG. 5, as the processing wheel rotates 210, the processing stations 212 operate to perform various operations, such as folding and sealing the individual blanks 118. As shown in FIG. 5, as the processing wheel rotates, the individual processing stations 212 move from the receiving location 214 to a folding location, which is generally represented by an arc 216. As discussed in more detail below, as the processing stations move along the folding location 216, the processing stations 212 actuate and fold the individual blanks 118 along one or more lateral axes 140, as discussed above with reference to FIGS. 1-3. As discussed in more detail below, the processing stations 212 may fold the blanks 118 in more than one direction, such as along one or more transverse axes 140 to form a U-shape of the absorbent article 100 and along the gripping areas 176, 178, 180, 182 to position the sealing areas 168, 170, 172, 174 for engagement.

As the processing wheel continues to rotate, the processing stations 212 move from the folding location 216 to a sealing location, generally represented in FIG. 5 by an arc 218. As the processing stations move along the sealing location 218, the processing stations engage the sealing areas 168, 170, 172, 174 on the blanks 118 to form side seams 122, 124 of absorbent articles 100, such as discussed above with reference to FIGS. 1-4e. The processing wheel 210 continues to rotate and the processing stations 212 move from the sealing location 218 to a discharge location 220, where the folded absorbent articles 100 are removed from the processing wheel 210. As the processing stations 212 move along the sealing location, the side seams are formed. As discussed above, the side seams may be formed with various types of connection methods, including for example, pressure bonding, ultrasonic bonding, heat sealing, adhesive attachment, and mechanical attachment. As such, in some arrangements, such as when forming absorbent articles with resealable side seams utilizing, for example, adhesives or mechanical attachments, pressure may be applied to the sealing area to form the side seams. In other arrangements, a heat exchanger and a compression tool may be used to form the side seams. In some embodiments, the heat exchanger forces hot air against the folded blanks, and the compression tool presses the side seams. In some embodiments, cool air may also be applied to the folded, seamed blanks to cool the blanks during compression. It is to be appreciated that depending on the particular configuration, heating and cooling times for the side seam material may vary. It should also be appreciated that FIG. 5 is schematic representation of an embodiment, and the positions and durations of some process steps may vary and/or may overlap, such as the receiving, folding, sealing, and discharge locations.

Figure 6A:
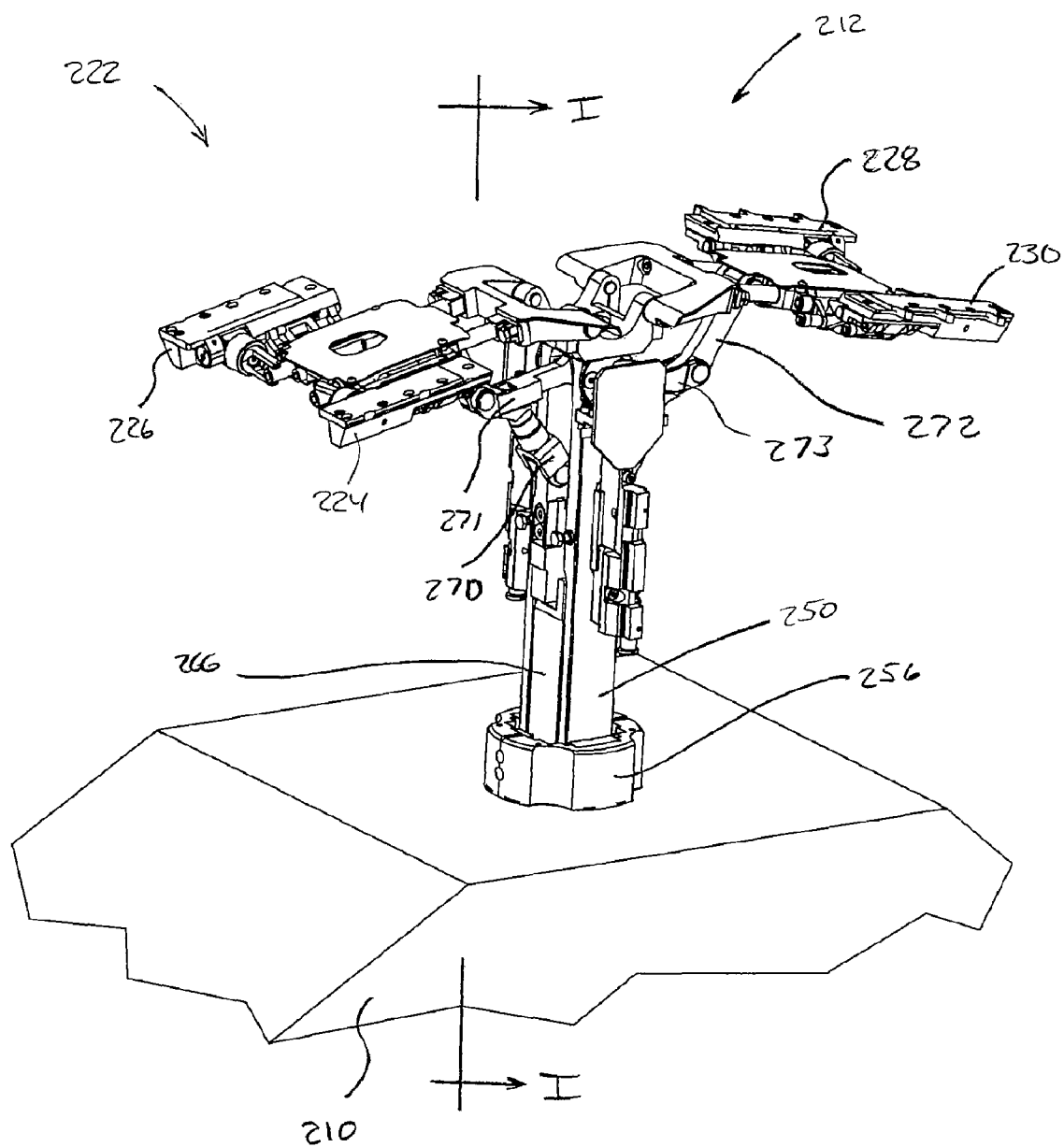
FIG. 6a is an isometric view of a processing station of a processing wheel.
Figure 6B:
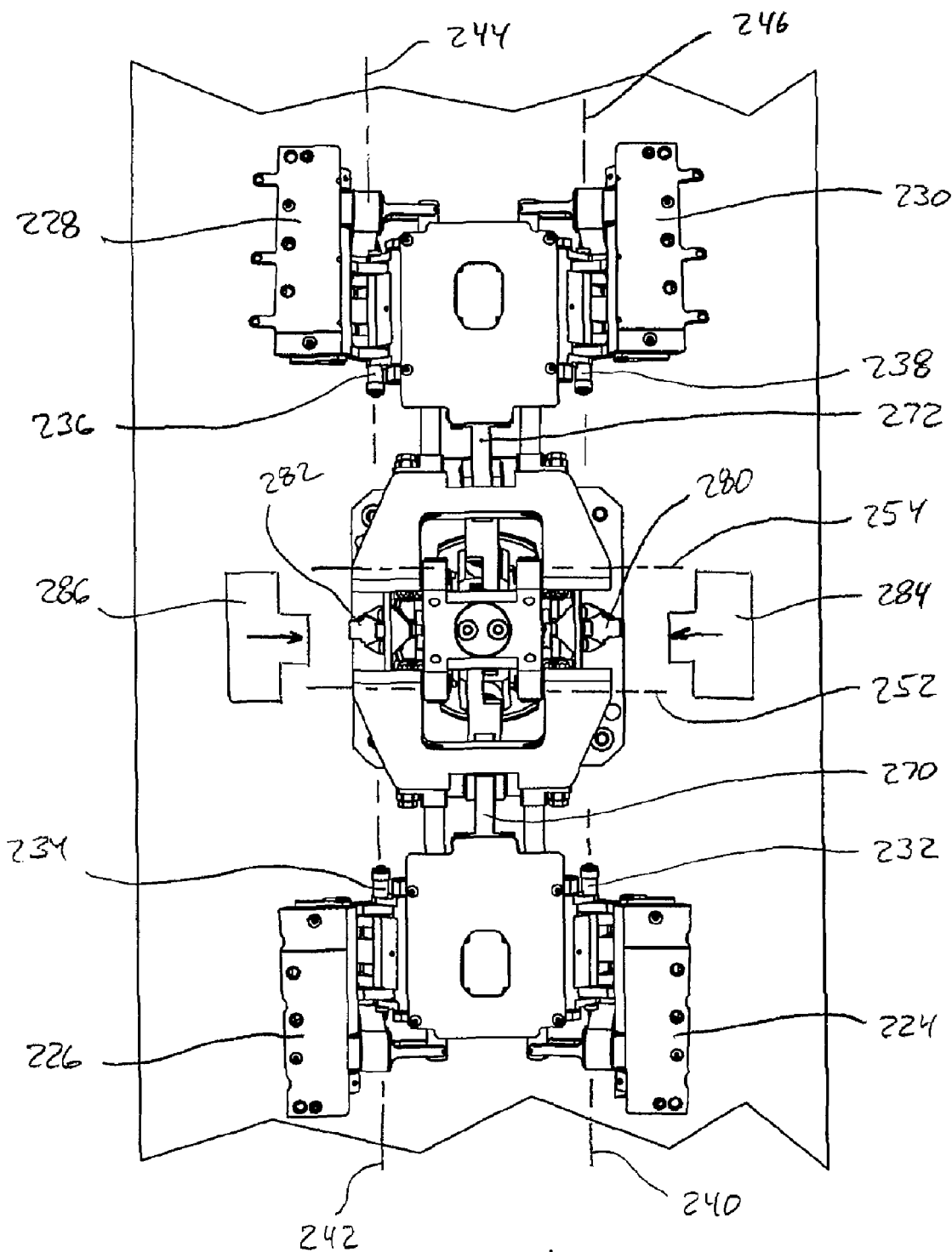
Figure 6C:
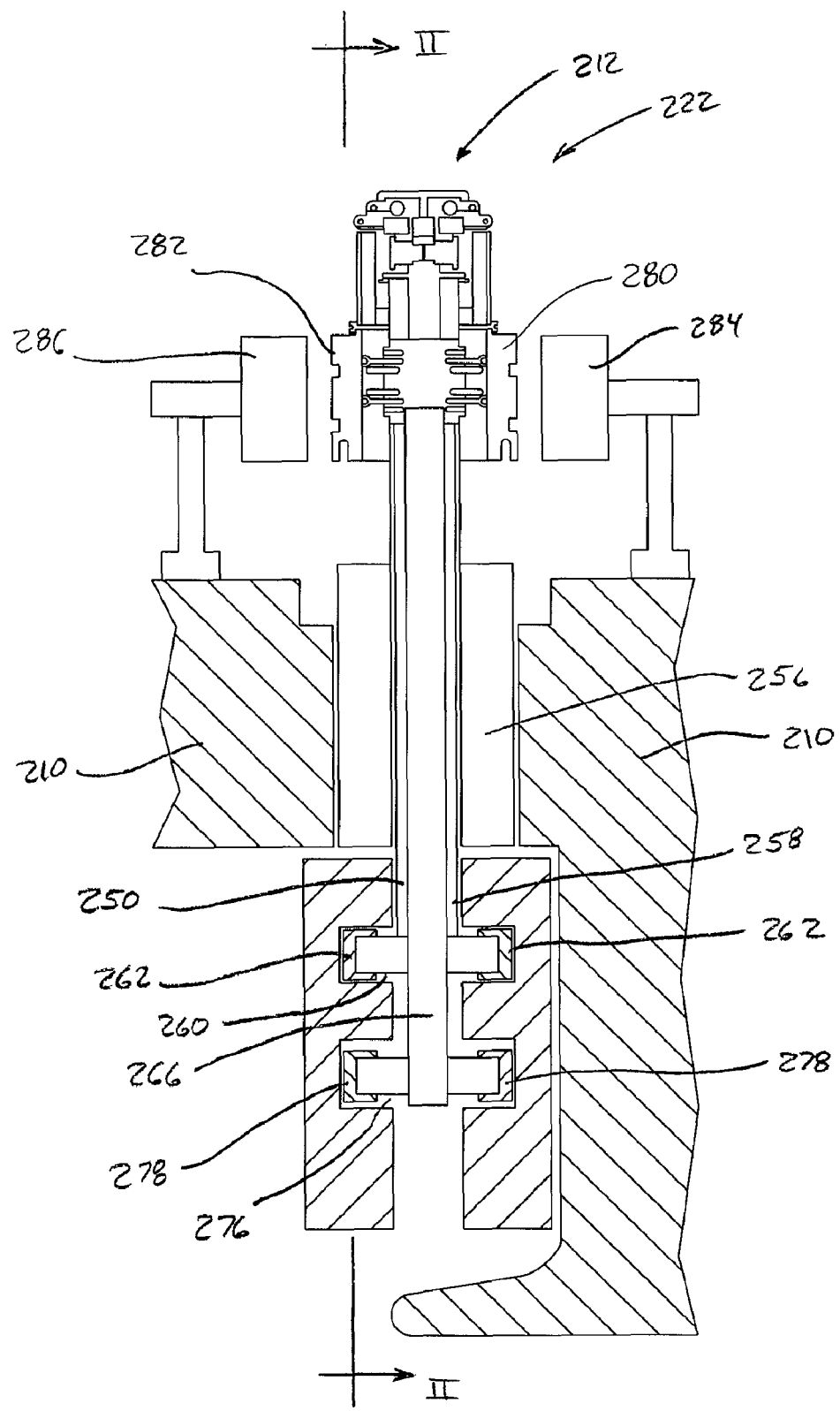
FIG. 6c is a partial cross sectional view of the processing wheel of FIG. 6a taken along line I-I.
Figure 6D:
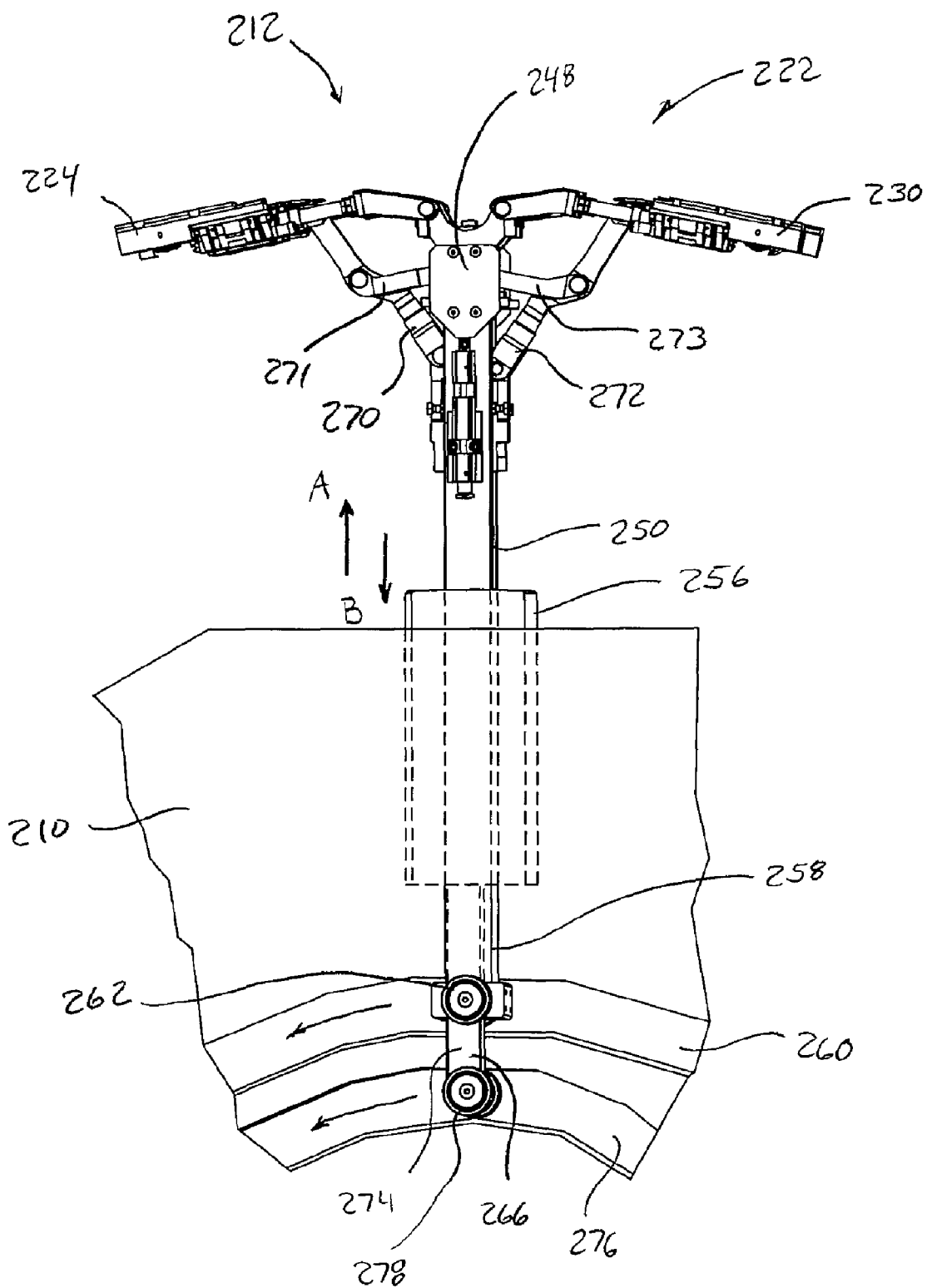
FIG. 6d is a partial cross sectional view of the processing wheel of FIG. 6c taken along line II-II.

As previously mentioned, the processing wheel includes a plurality of processing stations. For example, the processing wheel 210 shown in FIG. 5 includes nine processing stations 212. It should be appreciated that the processing wheel may include more or less processing stations than illustrated herein. For example, some embodiments may include six processing stations and some embodiments may include twelve processing stations. As discussed above, the processing stations 212 perform various operations as the processing wheel rotates. For example, individual blanks 118 disposed on respective processing stations 212 are folded as the processing wheel rotates. As such, each processing station 212 may include a folding mechanism upon which an individual blank is disposed as the processing wheel rotates. One embodiment of a folding mechanism 222 is shown in FIGS. 6a-6d. In particular, FIG. 6a shows a detailed view of the folding mechanism 222 on the processing wheel, FIG. 6b shows a top view of the folding mechanism 222; FIG. 6c shows a cross sectional view of the folding mechanism and processing wheel shown in FIG. 6a taken along line I-I; and FIG. 6d shows a cross sectional view of the folding mechanism and processing wheel shown in FIG. 6c taken along line II-II.

As shown in FIGS. 6a and 6b, the folding mechanism 222 includes gripper members 224, 226, 228, 230 which hold the blank 118 while the process wheel 210 rotates. More particularly, with reference to FIGS. 3-6d, the individual blanks 118 are transferred from the final station to the holding mechanism such that the grippers member 224, 226, 228, 230 are brought into contact with four respective gripping areas 176, 178, 180, 182 on the blanks 118. Each gripper may be configured with a vacuum that exerts a holding force on a respective gripping area of the blank. The gripper members are configured to rotate and move to fold the blanks 118.

As shown in FIGS. 6b and 6d, the folding mechanism 222 also includes carrier arms 232, 234, 236, 238 that rotatably support the gripper members 224, 226, 228, 230. As such, the gripper members are adapted to rotate about gripper axes 240, 242, 244, 246 at a distal end portion of the carrier arms. Proximal end portions of the carrier arms 232, 234, 236, 238 are pivotally connected to a distal end portion 248 of a first follower member 250. As such, the carrier arms 232, 234, 236, 238 are adapted to pivot about hinge axes 252, 254. From the distal end portion 248, the first follower member 250 extends through a hub member 256 to a proximal end portion 258. As such, the first follower member 250 is slidably connected with the hub member 256 and can move relative to the hub in directions "A" and "B" shown in FIG. 6d. The proximal end portion the first follower member 250 is operably connected with a first track 260 through one or more first rollers 262. As shown in FIGS. 6c and 6d, the first track 260 is stationary, and the hub member 256 is connected with and rotates with the processing wheel 210 along a path radially outward of the first track 260. Thus, as the processing wheel 210 rotates, the first track 260 remains stationary, the hub member 256 moves in a circular path about a rotation axis 264, and the first rollers roll 262 along the first track 260. As discussed in more detail below, depending on the path defined by the first track 260, the first follower member 250 may move radially inward and/or outward in direction A relative to the hub member 256 as the hub member moves in the circular path around the rotation axis 264.

As shown in FIGS. 6b and 6d, the folding mechanism 222 also includes a second follower member 266 that is operably connected with the first follower member 250 to pivot the carrier arms 232, 234, 236, 238 about the hinge axes 252, 254 as the processing wheel 210 rotates. More particularly, a distal end portion 268 of the second follower 266 member is pivotally connected with first end portions of connecting arms 270, 272. In turn, a second end portion of connecting arm 270 is pivotally connected with carrier arms 232, 234, and a second end portion of connecting arm 272 is pivotally connected with carrier arms 236, 238. Distance control arms 271, 273 may also be provided. Opposing end portions of the distance control arms 271, 273 may be pivotally connected with the first follower member 250 and the connecting arms 270, 272.

Figure 6E:
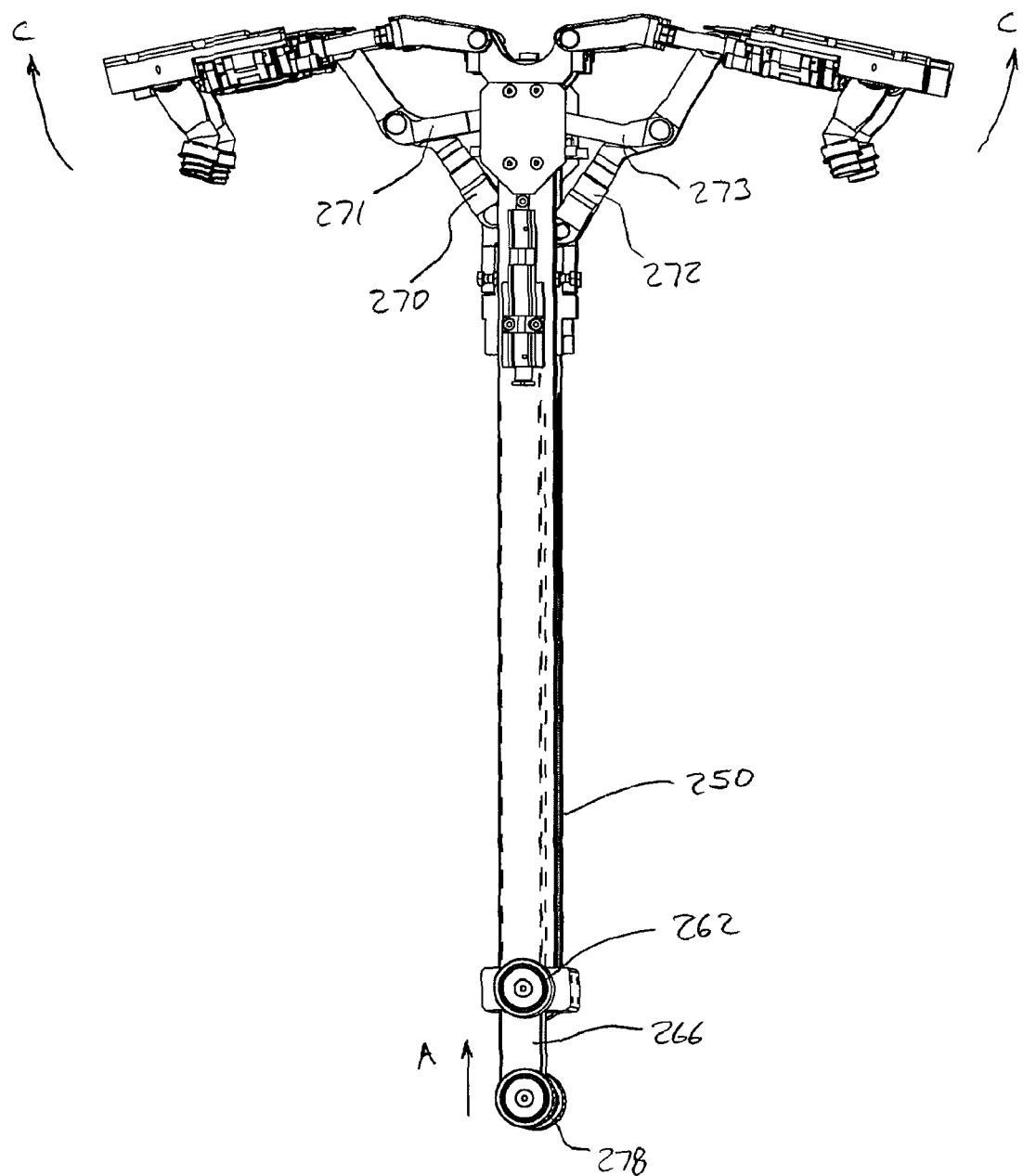
FIG. 6e is a view of a folding mechanism in an extended position.
Figure 6F:
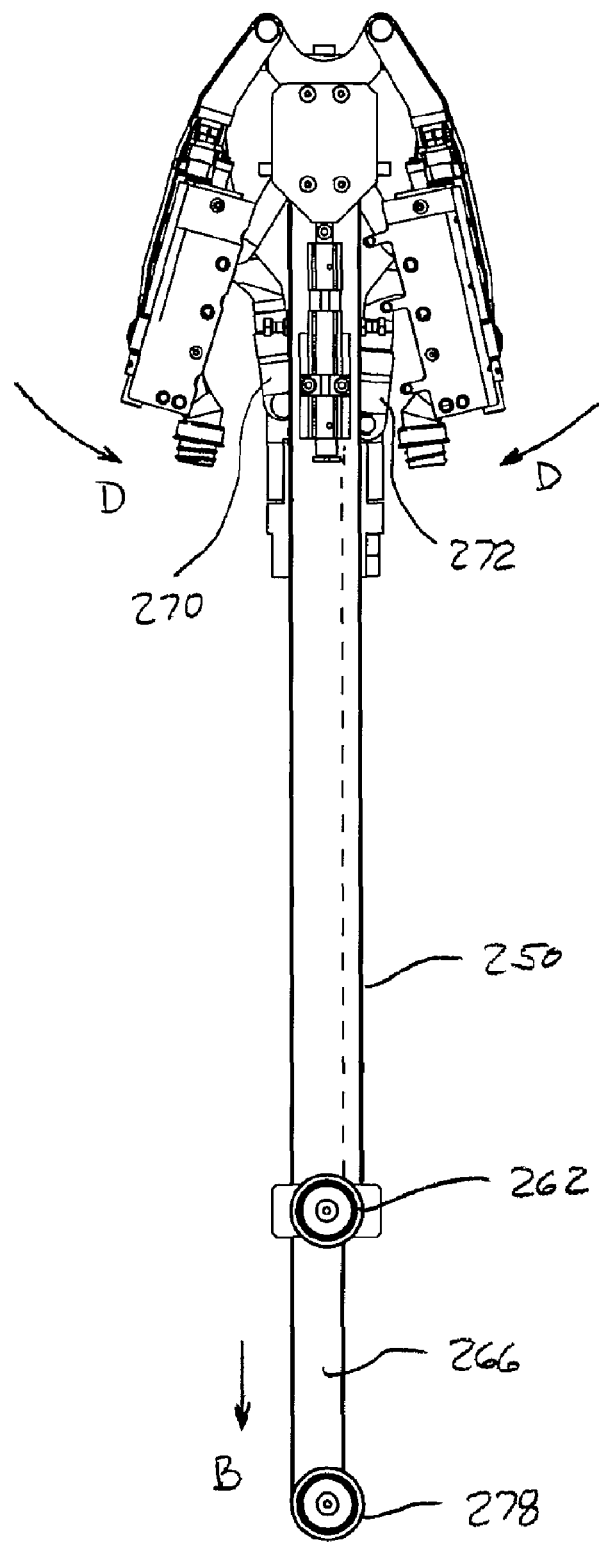
FIG. 6f is a view of a folding mechanism in a retracted position.

From the distal end portion 268, the second follower member 266 extends through a hollow interior of the first follower member 250 and the hub member 256 to a proximal end portion 274. As such, the second follower member 266 is telescopically connected with the first follower member 250 and can move relative to the first follower member in the directions A and B shown in FIG. 6d. The proximal end portion 274 the second follower member 268 is operably connected with a second track 276 through one or more second rollers 278. As shown in FIG. 6d, the second track 276 is stationary and defines a path radially inward of the first track 260. The hub member 256 is connected with and rotates with the processing wheel 210 radially outward of the second track 276. Thus, as the processing wheel 210 rotates, the second track 276 remains stationary, the hub member 256 moves in a circular path about the rotation axis 264, and the second rollers 278 roll along the second track 276. As discussed in more detail below, depending on a path defined by the second track 276 relative to the first track 260, the second follower member 266 may move radially inward and/or outward relative to the first follower member 250 as the hub member 256 moves in the circular path around the rotation axis 264. As such, movement of the second follower member 266 in a radially outward direction A relative to the first follower member 250 causes the second follower member 266 and connecting arms 270, 272 to push the carrier arms 232, 234, 236, 238 to pivot in direction C shown in FIG. 6e toward an extended position. FIG. 6e shows the folding mechanism 222 in an extended position. In contrast, movement of the second follower member 266 in a radially inward direction B relative to the first follower member 250 causes the second follower member 266 and connecting arms 270, 272 to pull the carrier arms to pivot in direction shown in FIG. 6f toward a retracted position or folding position. FIG. 6f shows the folding mechanism 222 in a retracted position or folding position.

It is to be appreciated the first and/or second follower members can be configured with only one roller and may also have various types of components other than rollers. For example, some embodiments may be configured various types of rolling contact elements, such as for example, ball bearings. Other embodiments may include pins that move along slotted tracks. In yet other embodiments, the follower members may configured with slots or voids that are adapted to receive and move along a protruding track.

As discussed above with reference to FIGS. 6a-6d, the gripper members 224, 226, 228, 230 are adapted to move and to fold the individual blanks 118 as the processing wheel 210 rotates. As previously described, the gripper members 224, 226, 228, 230 may be rotatably mounted on carrier arms 232, 234, 236, 238, and are adapted to be rotated about gripper axes 240, 242, 244, 246. The carrier arms 232, 234, 236, 238, in turn, are connected to first follower member 250 and can each be rotated around the hinge axes 252, 254. The hinge axes 250, 252 extend generally perpendicular to the rotational travel of the processing wheel 210 and generally perpendicular to the carrier arms 232, 234, 236, 238. Folding of the blank 118 occurs at the folding area 216 of the processing wheel 210, as indicated in FIG. 5. Folding of the blank 118 may occur in two directions: (1) along one or more transverse axes 140 to form a U-shape of the absorbent article 100; and (2) along the gripping areas 176, 178, 180, 182 to position the sealing areas 168, 170, 172, 174 for engagement. In some configurations, the gripper members may be rotatably connected with the carrier arms through a helical or barrel cam arrangement that allows the gripper members to move linearly along the length of the carrier arms as the carrier arms pivot. Such movement allows the gripper members to maintain a relatively constant position of the grippers on the blank as the blank is folded while at the same time avoiding the stretching of the blank.

As shown in FIGS. 6b and 6c, the first follower member 250 includes anvils 280, 282 on opposing sides of the distal end portion 248 of the first follower member. In addition, seaming heads 284, 286 are mounted on the processing wheel adjacent the anvils 280, 282. More particularly, the seaming heads 284, 286 are connected with support arms 288, 290 that are pivotally connected with the processing wheel 210. As the processing wheel rotates through the folding location 218, the support arms 288, 290 pivot to place the seaming heads 284, 286 in close proximity to the anvils 280, 282 while the sealing operation is carried out. As the processing wheel continues to rotate, the support arms 288, 290 pivot in an opposite direction to move the seaming heads 284, 286 away from the anvils 284, 286. The movement of the support arms and seaming heads can be accomplished in various ways. For example, in one embodiment, the support arms engage a cam surface that causes the carrier arms to pivot a particular distance and for a particular portion of the processing wheel's rotation.

FIG. 6b shows an individual blank disposed on a folding mechanism 222 an extended position. As such, the gripping areas 176, 178, 180, 182 of the blank are disposed on respective gripper members 224, 226, 228, 230. As the processing wheel 210 rotates through the folding location 216 shown in FIG. 5, the folding mechanism 222 retracts to the folding position by pivoting the carrier arms 232, 234, 236, 238 about the hinge axes 252, 254 in direction D shown in FIG. 6f. In addition, each gripper member 224, 226, 228, 230 may rotate about the gripper axes 240, 242, 244, 246 to place the sealing areas 168, 174 and 170, 172 of the blank 118 an overlapping relationship. As the processing wheel 210 rotates from the folding location 216 into the sealing location 218, the overlapped sealing areas 168, 174 and 170, 172 are located adjacent anvils 280, 282 on the first follower member 250. Seaming heads 284, 286 then move to press the overlapped sealing areas 168, 174 and 170, 172 against each other between the anvils 280, 282 and the seaming heads 284, 286, which in turn, seal the overlapped sealing areas 168, 174 and 170, 172 with one another. As the processing wheel 210 continues through the sealing location, the seaming heads 284, 286 retract and move away from the overlapped sealing areas 168, 174 and 170, 172, having created overlapping side seams 126, 128 of an absorbent article 100 as shown for example in FIGS. 1 and 1a.

Figure 7A:
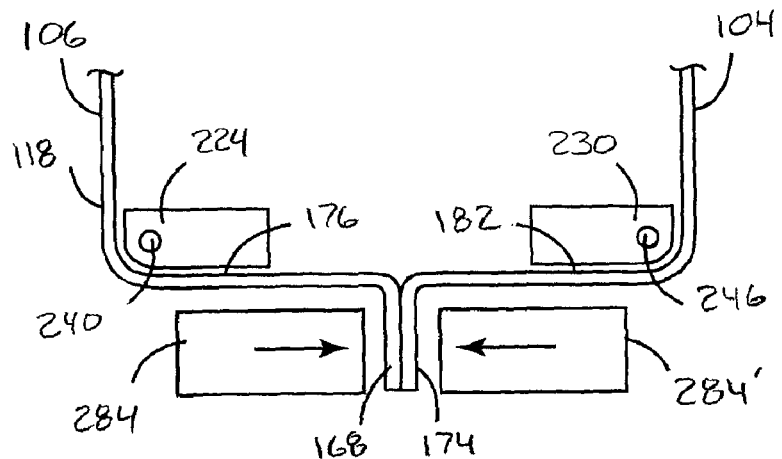
FIG. 7a shows a schematic top view of a gripper and sealer in formation of a butt-type side seam.

It should be appreciated that the folding station 222 can also be configured to create butt-type seams 130, 132 such as shown in FIGS. 2 and 2a. Thus, instead of overlapping the sealing areas 168, 174 and 170, 172, the gripper members 224, 226, 228, 230 may be simultaneously rotated around the respective gripper axes 240, 242, 244, 246 such that the sealing areas 168, 174 and 170, 172 mutually abut and extend generally perpendicular outward from the first follower member 250. Sealing may then occur by pressing the abutting sealing areas 168, 174 and 170, 172 between two seaming heads. For example, FIG. 7a shows two seaming heads 284, 284' pressing sealing areas 168, 174 together in an abutting relationship.

Figure 7B:
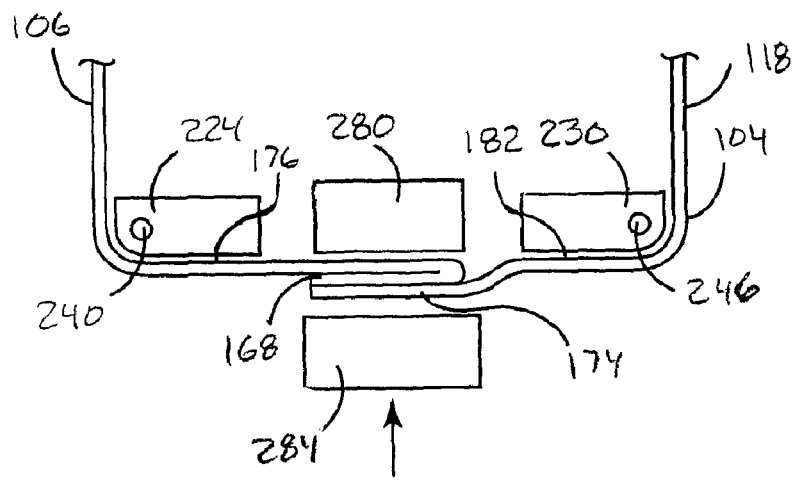
FIG. 7b shows a schematic top view of a gripper and sealer in formation of a combined overlapping and butt-type side seam.
Figure 7C:
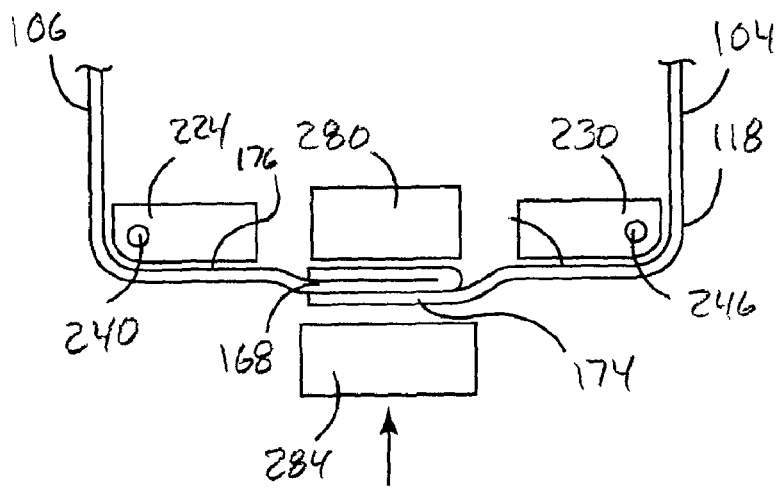
FIG. 7c shows a schematic top view of a gripper and sealer in formation of a three-layer overlapping side seam.

Depending on the configuration of the folding station 222 and associated parts, different embodiments of overlapping and abutting side seams can be created, such as for example, shown in FIGS. 7b and 7c. In the embodiment of FIG. 7b, a side seam is formed as a combination of a butt-type seam such as shown in FIG. 2 and an overlapping seam such as shown in FIG. 1. The seam of FIG. 7b can be formed by first placing the sealing areas 168, 174 in an abutting relationship as shown in FIG. 7a, and then folding over the abutting sealing areas. The folded-over abutting sealing areas 168, 174 may then be compressed between the seaming head 284 and the anvil 280. FIG. 7c shows an overlapping seam comprising three layers of material. In this embodiment, the sealing area 168 is folded over before being placed in a superimposed relationship with the sealing area 174.

It is to be appreciated that various types and configurations of seaming heads and anvils may be used to create the side seams on the absorbent articles. As discussed above, the side seams may be formed with various types of connection methods, including for example, pressure bonding, ultrasonic bonding, heat sealing, adhesive attachment, and mechanical attachment. As such, in some arrangements, such as when forming absorbent articles with resealable side seams utilizing, for example, adhesives or mechanical attachments, the seaming heads may act only to apply pressure to the sealing areas to form the side seams. In another example, the seaming heads may comprise heated elements that contact the anvils under any pressure. In some embodiments, the pressure may be in the range of from about 1 psi to about $10^4$ psi. In other embodiments, side seaming may utilize with hot air. In one example, a heat exchanger is brought close to overlapping material of the blank and blows hot air against the blank. After applying the hot air, seaming heads compress the overlapping sides. Thus, the material of the side portions is heated and compressed to form the side seal. In yet another embodiment, the seaming heads comprise an ultrasonic conductor. The ultrasonic energy imparted to the sealing areas puts the thermoplastic material of the sealing areas in a heat-softened state, such that upon compression of the sealing areas between the anvil and the conductors an overlapping side seam is formed.

Although the above discussion presents a detailed discussion of embodiments of the processing and folding stations, it is to be appreciated that other embodiments of processing stations that may be adapted for use with the methods and apparatuses disclosed herein. For example, U.S. Pat. No. 7,322,925, U.S. Pat. No. 5,779,831, and U.S. Patent Publication No. 2008083489A1 provide descriptions of various embodiments of processing and folding stations that can be adapted for use with the methods and apparatuses disclosed herein.

As shown in FIG. 6b, the folding mechanism 222 defines a length, $L_{STATION}$, between distal end portions of the gripper members 224, 226, 228, 230. The length, $L_{STATION}$, corresponds with the length, $L_{BLANK}$, of the blanks 118 discussed above with reference to FIG. 3. As such, the geometry of the processing stations 212 and folding mechanisms 222 may be adapted to accommodate the length of the blanks 118 being manufactured. For example, a length, $L_{BLANK}$, defined by relatively large absorbent articles may require the folding mechanism to define a corresponding length, $L_{STATION}$, that is relatively long. In another example, a length, $L_{BLANK}$, defined by relatively small absorbent articles may require the folding mechanism to define a corresponding length, $L_{STATION}$, that is relatively short. Thus, depending upon the length of the blanks to be manufactured, the folding mechanisms on the processing wheel may be changed to define shorter or longer lengths, $L_{STATION}$. In turn, the first track 260 and/or second track 276 may be changed to define different shapes to accommodate the changed geometry of the folding stations.

Figure 8B:
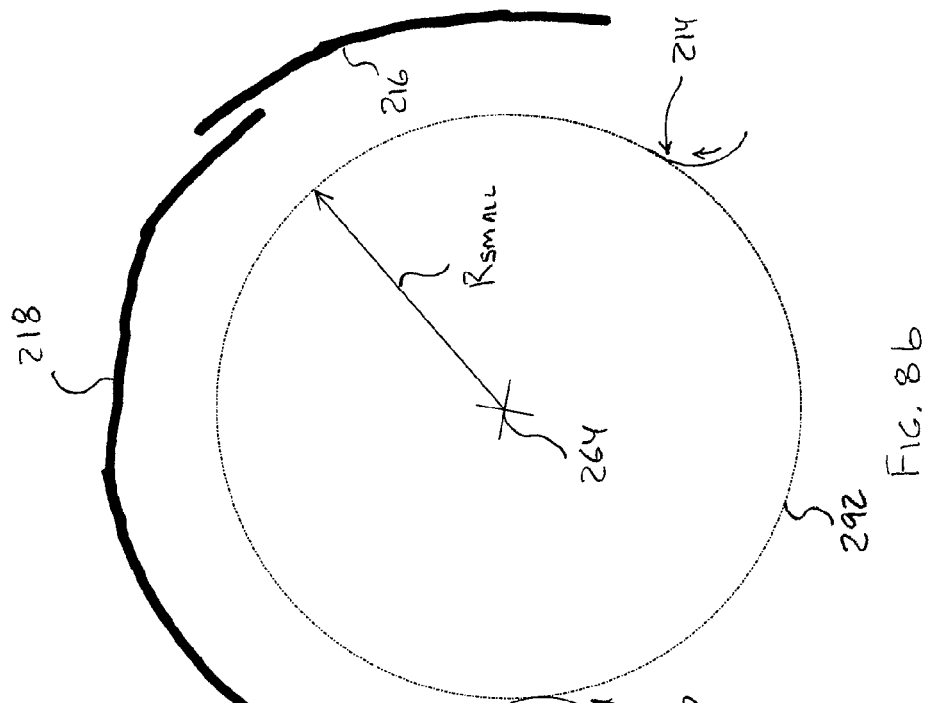
Figure 8A:
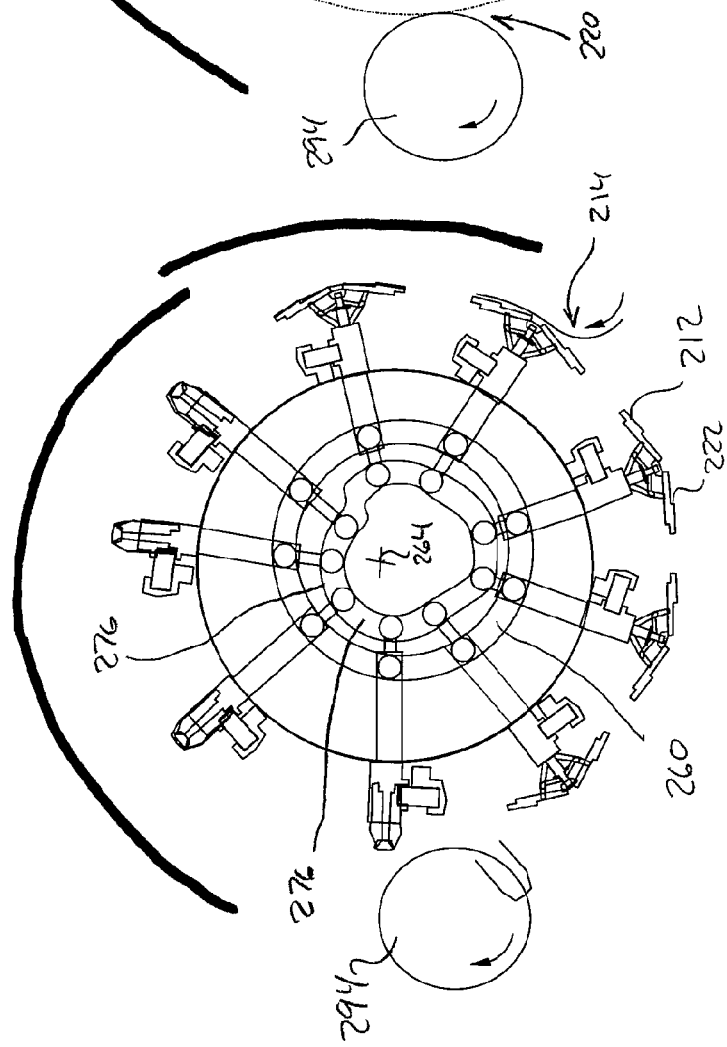
FIG. 8a is a schematic side view of a processing wheel configured for folding and seaming relatively small size blanks.

In one example, FIG. 8a shows a schematic representation of a processing wheel 210 and folding stations 212 configured for the manufacture of relatively small blanks 118 (i.e. relatively short $L_{BLANK}$). As the processing wheel rotates around the rotation axis 264, the processing stations 212 and folding mechanisms 222 move from the receiving location 214, through the folding location 216 and the sealing location 218, to the discharge location 220, and around to the receiving location 214. Thus, the distal end portion 248 of the first follower member 250 travels along an orbit path 292 shown in FIG. 8b. As discussed above, during rotations of the processing wheel 210, the first rollers 262 roll along the first track 222. As such, radial inward and outward movements of the folding mechanisms 222 relative to rotation axis 264 are dictated by the circumferential shape of the first track 260. As shown in FIG. 8a, the first track 260 defines a circular circumferential shape. Thus, as the distal end portions 248 of the first follower members 250 travel along a circular-shaped orbit path 292 having a constant distance $R_{SMALL}$ from the rotation axis 264.

Figure 9B:
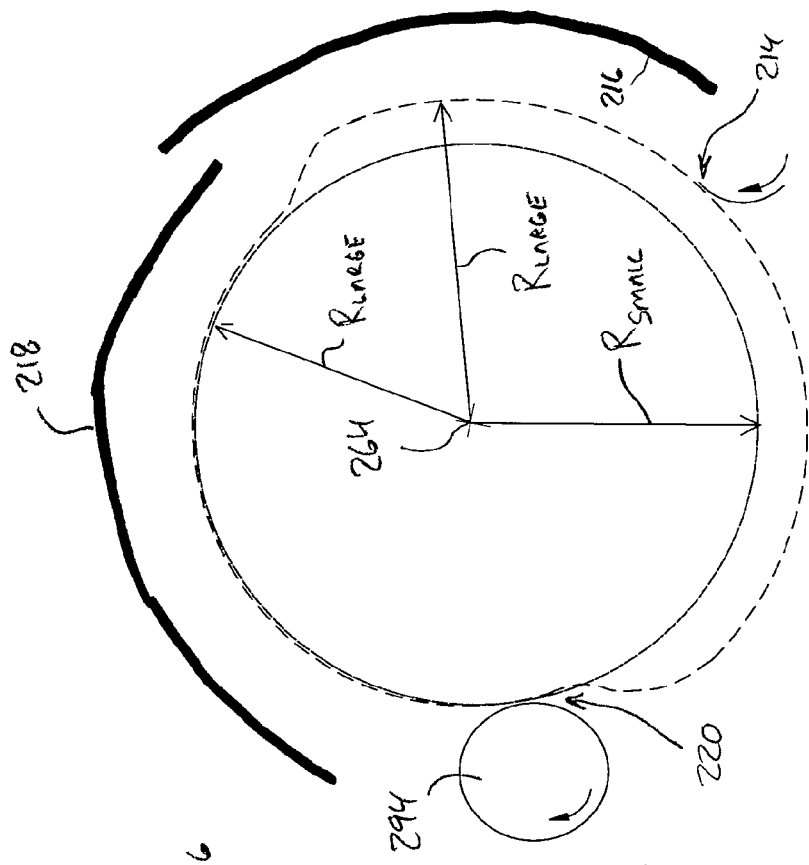
Figure 9A:
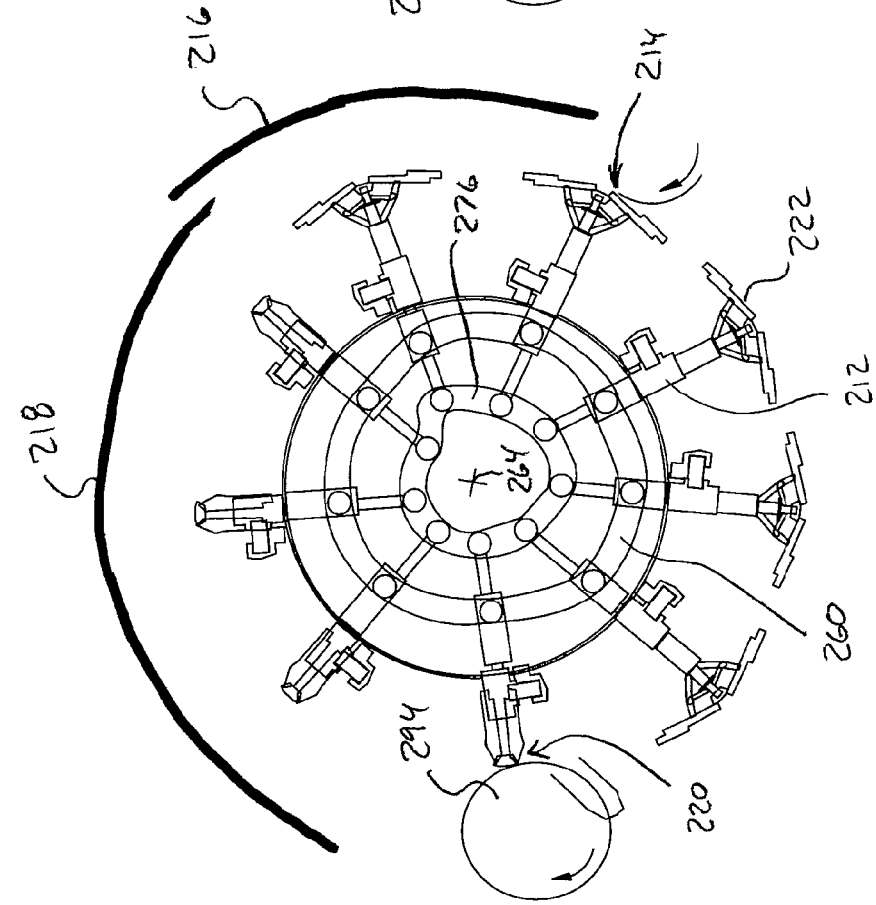
FIG. 9a is a schematic side view of a processing wheel configured for folding and seaming relatively large size blanks.

FIGS. 9a and 9b illustrate an example of how the processing wheel 210 can be reconfigured to accommodate relatively larger blanks 118 as compared to the processing wheel configuration of FIGS. 8a and 8b. In particular, FIG. 9a shows a schematic representation of a processing wheel 210 and folding stations 212 configured for the manufacture of relatively large blanks 118 (i.e. relatively long $L_{BLANK}$). Again, as the processing wheel rotates around the rotation axis 264, the processing stations 212 and folding mechanisms 222 move from the receiving location 214, through the folding location 216 and the sealing location 218, to the discharge location 220, and around to the receiving location 214. Thus, the distal end portion 248 of the first follower member 250 travels along orbit path 292 shown in FIG. 9b. As discussed above, during rotations of the processing wheel 210, the first rollers 262 roll along the first track 222. As such, radial inward and outward movements of the folding mechanisms 222 relative to rotation axis 264 are dictated by the circumferential shape of the first track 260. Thus, as the distal end portions 248 of the first follower members 250 travel along a circular-shaped orbit path 292 having a variable distance $R_{LARGE}$ from the rotation axis 264. However, the circumferential shape of the first track 260 shown in FIG. 9a is different than the first track shown in FIG. 8a. More particularly, the first track 260 in FIG. 9a is shaped such that the distal end portions 248 of the first follower members 250 move radially outward from the rotation axis 264 as the folding stations move past the discharge location 214 and until moving into the sealing location 218. Once the folding stations 222 move into sealing location 218, the distal end portions 248 of the first follower members 250 move inward toward the rotation axis 264 until after the discharge location 220. Thus, the distal end portion 248 of the first follower member 250 travels along an orbit path 292 shown in FIG. 9b.

As previously mentioned, the apparatuses and methods according to the present disclosure provide flexibility in reconfiguring the processing wheel to fold and seam different sizes of absorbent articles. For example, the processing wheel configuration shown in FIG. 9a allows the folding mechanisms 222 to be geometrically modified to have relatively longer $L_{STATION}$ without having to make corresponding modifications to other equipment and operations associated with the processing wheel 210. For instance, the shape of the first track 260 causes the distal end portions 248 of the first follower members 250 to move outwardly from the rotation axis 264 while the folding mechanisms 222 are in an extended position, such as shown in FIG. 6e. The outward movement of the distal end portions 248 allow folding mechanisms 222 having a relatively long $L_{STATION}$ dimensions to move to extended positions without interfering with adjacent folding mechanisms 222. In contrast, once the folding mechanisms 222 move to retracted positions, such as shown in FIG. 6f, the shape of the first track 260 causes the distal end portions 248 of the first follower members 250 to move inwardly toward the rotation axis 264. The shape of the first track 262 can be configured such that the first follower members 250 are moved to the same radial position relative to the rotation axis 264 in FIG. 9a during the sealing operation as in FIG. 8a. As such, the geometry of the folding mechanisms 222 can be adjusted to accommodate different sized blanks 118 without having to remove, reinstall, and realign the various parts, such as the anvils 280, 282 and/or sealers 284, 286.

In another example, comparing FIGS. 8a and 9a, the first track 260 defines a shape that allows the folding stations 222 to accommodate different sized blanks 118 without having to move the discharge location 220 closer to or farther away from the rotation axis 264 of the processing wheel 210. For example, as shown in FIGS. 8a and 9a, blanks 118 are discharged from the processing wheel 210 to another mechanism, in the form of a vacuum roller 294, at the discharge location 220. The folding stations 222 can be geometrically modified to accommodate different sized blanks 118 without having to physically move and realign the vacuum roller 294 with the processing wheel 210. It should also be appreciated that the first track 260 can be configured in different shapes than what are shown and described herein. For example, the first track 260 can be modified to define an orbit path 292 having straight portions. In one embodiment, the orbit path is configured with a straight portion near the discharge location 220 when discharging the blanks 118 onto a flat conveyor, as opposed to a vacuum roll. In other examples, the first track 260 can be configured to define an orbit path 292 wherein the distal end portions 248 of the first follower members 250 move radially outward from the rotation axis 264 when transitioning from the folding location 216 to the sealing location 218.

As previously discussed, it is to be appreciated that other embodiments of processing stations that may be adapted for use with the methods and apparatuses disclosed herein, such as disclosed for example in U.S. Pat. No. 7,322,925, U.S. Pat. No. 5,779,831, and U.S. Patent Publication No. 2008083489A1. As such, it is contemplated that other processing station configurations may utilize folding mechanisms that are actuated in various ways without utilizing relative positions between first and second tracks as discussed above.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An apparatus for making absorbent articles having side seams, the apparatus comprising:
   a wheel adapted to rotate about a rotation axis;
   a first track defining a first circumferential shape surrounding the rotation axis and having a varying distance from the rotation axis, wherein the first track is stationary relative to the wheel;
   a second track defining a second circumferential shape surrounding the rotation axis and having a varying distance from the rotation axis, wherein the second track is stationary relative to the wheel;
   a plurality of folding mechanisms disposed on the wheel, each folding mechanism comprising:
   a first follower member movably connected with the first track, the first follower member having a proximal end portion and a distal end portion;
   a carrier arm pivotally connected with the first follower member;
   a gripper member connected with the carrier arm;
   a second follower member connected with the carrier arm and movably connected with the second track; and
   wherein as the wheel rotates, the distal end portion of the first follower member orbits in a first orbit path about the rotation axis in correspondence with the first circumferential shape; and
   wherein as the wheel rotates, the second follower member moves relative to the first follower member in correspondence with a relative radial distance between the first track and the second track.

2. The apparatus of claim 1, wherein the first orbit path is partially defined by a curved portion and a straight portion.

3. The apparatus of claim 1, further comprising a first roller connected with the proximal end portion of the first follower member, and wherein the first roller is rollingly engaged with the first track.

4. The apparatus of claim 3, further comprising a second roller connected with a proximal end portion of the second follower member, and wherein the second roller is rollingly engaged with the second track.

5. The apparatus of claim 1, further comprising a seamer member adapted to periodically engage the first follower member as the wheel rotates.

* * * * *